(12) United States Patent
Vogt et al.

(10) Patent No.: US 11,998,451 B2
(45) Date of Patent: Jun. 4, 2024

(54) DEVICE AND METHOD FOR PRODUCING SPACERS

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 387 days.

(21) Appl. No.: 17/205,221

(22) Filed: Mar. 18, 2021

(65) Prior Publication Data
US 2021/0290396 A1 Sep. 23, 2021

(30) Foreign Application Priority Data

Mar. 20, 2020 (EP) .................................. 20164534
Apr. 24, 2020 (EP) .................................. 20171303

(51) Int. Cl.
*B29C 45/32* (2006.01)
*A61F 2/30* (2006.01)
(Continued)

(52) U.S. Cl.
CPC ...... *A61F 2/30942* (2013.01); *A61F 2/30724* (2013.01); *A61F 2/32* (2013.01);
(Continued)

(58) Field of Classification Search
CPC ........ A61F 2/30942; A61F 2/46; B29C 45/38; B29C 45/23
See application file for complete search history.

(56) References Cited

U.S. PATENT DOCUMENTS 2,842,798 A * 7/1958 Paschold ................. B29C 45/38
  425/DIG. 51
5,681,289 A 10/1997 Wilcox et al.
(Continued)

FOREIGN PATENT DOCUMENTS

CN 201335161 Y * 10/2009
DE 102015104704 B4 10/2016
(Continued)

*Primary Examiner* — Cachet I Proctor
(74) *Attorney, Agent, or Firm* — Dicke, Billig & Czaja, PLLC

(57) ABSTRACT

The invention relates to a device for producing a spacer having a casting mold with at least one filling opening, a valve seat, which is connected to the casting mold, wherein the valve seat has an regionally closed head side with at least one first feed-through, a valve body which is mounted so as to be rotatable relative to the valve seat and which has a sealing face, wherein at least one second feed-through is arranged in the sealing face, wherein the valve seat and the valve body together form a valve, wherein the valve is reversibly transferable into an open position and a closed position by rotation of the valve body relative to the valve seat, wherein, in the open position of the valve, the at least one first feed-through of the valve seat and the at least one second feed-through of the valve body are located above one another at least in places and provide a permeable connection through the valve into the casting mold, wherein, in the closed position of the valve, the at least one first feed-through of the valve seat is covered by the sealing face of the valve body, wherein, in the closed position of the valve, the at least one filling opening of the casting mold is covered and wherein the valve is connected on the side remote from the casting mold to a port for liquid-tight connection of a bone cement cartridge or the valve has such a port. The invention also relates to a method for producing spacers using such a device.

29 Claims, 28 Drawing Sheets

(51) Int. Cl.
  *A61F 2/32*  (2006.01)
  *A61F 2/40*  (2006.01)
  *B29C 45/34* (2006.01)
  *B29C 45/00* (2006.01)
  *B29K 33/00* (2006.01)

(52) U.S. Cl.
  CPC ............... *A61F 2/40* (2013.01); *B29C 45/34* (2013.01); *A61F 2002/30672* (2013.01); *A61F 2002/30957* (2013.01); *A61F 2310/00353* (2013.01); *B29C 45/0001* (2013.01); *B29K 2033/12* (2013.01)

(56) References Cited

U.S. PATENT DOCUMENTS

| | | | |
|---|---|---|---|
| 6,245,111 | B1 | 6/2001 | Shaffner |
| 6,309,208 | B1* | 10/2001 | Kazmer ............. B29C 45/1603 425/562 |
| 6,361,731 | B1* | 3/2002 | Smith ................ B29C 33/405 264/318 |
| 7,637,729 | B2 | 12/2009 | Hartman et al. |
| 7,789,646 | B2 | 9/2010 | Haney et al. |
| 8,480,389 | B2 | 7/2013 | Haney et al. |
| 8,801,983 | B2 | 8/2014 | Haney et al. |
| 8,900,322 | B2 | 12/2014 | De Beaubien |
| 9,433,506 | B2* | 9/2016 | Lomicka ............... A61F 2/38 |
| 11,154,343 | B2* | 10/2021 | Vogt ..................... A61L 24/043 |
| 11,255,463 | B2* | 2/2022 | Thurau ................ F16K 41/046 |
| 2003/0056931 | A1* | 3/2003 | Wuthrich ............ B22D 17/145 164/410 |
| 2007/0222114 | A1 | 9/2007 | Ziran et al. |
| 2008/0058950 | A1 | 3/2008 | Leonard et al. |
| 2009/0146342 | A1* | 6/2009 | Haney ..................... A61F 2/32 425/111 |
| 2009/0175978 | A1* | 7/2009 | Hawkins ................ A61F 2/36 425/470 |
| 2010/0042213 | A1 | 2/2010 | Nebosky et al. |
| 2011/0015754 | A1 | 1/2011 | Leonard et al. |
| 2011/0272437 | A1* | 11/2011 | Vogt .................. B05C 17/00553 222/389 |
| 2013/0187310 | A1* | 7/2013 | Vogt ......................... A61F 2/36 264/313 |
| 2013/0344186 | A1 | 12/2013 | Haney et al. |
| 2014/0077115 | A1* | 3/2014 | Vogt ....................... A61M 39/22 251/304 |
| 2014/0159282 | A1* | 6/2014 | Smith .................. B29C 45/0001 425/589 |
| 2014/0348973 | A1* | 11/2014 | Holt ........................ B29C 48/03 425/542 |
| 2016/0332328 | A1 | 11/2016 | Wüst et al. |
| 2017/0333191 | A1* | 11/2017 | Foroni .................... A61F 2/3094 |
| 2018/0289406 | A1* | 10/2018 | Vogt .................. A61B 17/8833 |
| 2019/0290833 | A1* | 9/2019 | Vogt ........................ A61F 2/36 |
| 2020/0009771 | A1* | 1/2020 | Smith ................... A61F 2/4684 |
| 2021/0016595 | A1* | 1/2021 | Maresh ................ B43K 5/005 |

FOREIGN PATENT DOCUMENTS

| | | |
|---|---|---|
| DE | 102017107569 A1 | 10/2018 |
| EP | 2522310 A1 | 11/2012 |
| EP | 2617393 B1 | 7/2015 |
| EP | 1991170 B1 | 10/2016 |
| EP | 2787928 B1 | 7/2017 |
| EP | 3245981 A1 | 11/2017 |
| WO | 2009/073781 A2 | 6/2009 |
| WO | 2013/086177 A1 | 6/2013 |
| WO | 2016/205077 A1 | 12/2016 |
| WO | 2017/125832 A1 | 7/2017 |
| WO | 2017/178951 A1 | 10/2017 |
| WO | 2018/203150 A1 | 11/2018 |

* cited by examiner

DEVICE AND METHOD FOR PRODUCING SPACERS

CROSS-REFERENCE TO RELATED APPLICATIONS

This application claims priority to European Patent Application No. 20171303.9 filed on Apr. 24, 2020, and European Patent Application No. 20164534.8 filed on Mar. 20, 2020, the entire disclosures of which are incorporated by reference herein.

BACKGROUND

The invention relates to a device for producing a spacer by curing bone cement paste. The spacer is provided as a temporary placeholder in medical applications for temporarily replacing a joint or part of a joint comprising an articulating surface of the joint. The spacer is preferably suitable and provided for temporarily replacing a hip joint or a shoulder joint. The device is accordingly preferably provided for producing a hip joint spacer or a shoulder joint spacer. The invention also relates to a method for producing such a spacer using such a device.

Joint endoprostheses, such as hip joint endoprostheses and shoulder joint endoprostheses, are widely implanted worldwide. Unfortunately, in a small percentage of cases, joint endoprostheses are colonized by microbial microorganisms, in particular Gram-positive bacteria and also Gram-negative bacteria, and to a very small extent by yeasts and fungi. These microbial microorganisms, mainly typical skin microbes such as *Staphylococcus aureus* and *Staphylococcus epidermidis*, may enter a patient's body during a surgical operation (OP). It is also possible for microbial microorganisms to enter joint endoprostheses hematogenically. Where joint endoprostheses are colonized by microbial microorganisms, the surrounding bone and soft tissue also become infected and damaged by the microbial microorganisms.

The prior art primarily encompasses two treatment methods for infected joint endoprostheses, one-stage septic revision and two-stage septic revision. In the case of one-stage revision, first of all the infected joint endoprosthesis is removed, next radical debridement is performed and then a revision joint endoprosthesis is implanted within one OP.

In two-stage septic revisions, in a first OP the infected joint endoprosthesis is initially removed, then debridement is performed and thereafter a spacer is implanted. A hip joint spacer consists of a stem, a collar, a neck and a ball head and replicates hip joint endoprostheses in shape and size. Similarly, a shoulder joint spacer replicates a shoulder joint endoprosthesis in shape and size. The spacer is anchored with bone cement to the respective bone, i.e. for example in the case of hip joint spacers to the proximal femur or in the femoral canal. The spacer remains for up to several weeks in the patient until the inflammation has subsided and clinical inflammation markers have receded. The spacer is then removed in a second OP and a revision joint endoprosthesis implanted after fresh debridement.

With spacers, antibiotics are added to the cement powder before actual spacer production. Using this antibiotically modified bone cement powder, a bone cement paste is then produced by admixing monomer liquid and spacers are cast from this bone cement paste which then cure by polymerization with the assistance of the monomer liquid added to the cement powder. The bone cement paste thus substantially encloses the antibiotics. The antibiotic particles situated in areas close to the surface are released under the action of bodily fluids, such as wound secretions. Active ingredient release is greatest at the start and then diminishes over the course of several days.

US 2010/0042213 A1 discloses a hip joint prosthesis with a reservoir for liquid inside the implant. A hip spacer is known from WO 2017/178951 A1 which has recesses, wherein a substance for treating the bone may be introduced into the recesses. U.S. Pat. No. 6,245,111 B1 proposes a hip joint prosthesis, the surfaces of which are coated with an antibiotic. U.S. Pat. No. 5,681,289 discloses a device for distributing a liquid active ingredient with the assistance of a bladder inside the device. None of the stated prostheses is suitable for producing an irrigation circuit. EP 1 991 170 B1 and US 2011/0015754 A1 describe a hip joint spacer containing active ingredients. US 2019/0290833 A1 discloses an irrigatable hip joint spacer, with which a liquid circuit is creatable. WO 2016/205077 A1 and U.S. Pat. No. 8,900,322 B2 describe further spacers with an irrigation function.

It is known to use spacers provided with antibiotics. Spacers may on the one hand be produced by the OP personnel during the OP itself from PMMA bone cement powder, antibiotics and monomer liquid, for example with a spacer mold, as described for example in patents DE 10 2015 104 704 B4 or EP 2 617 393 B1; on the other hand it is also conventional to use hip joint spacers prefabricated industrially from bone cement. Resin casting molds for intraoperative production of one-part hip spacers are described in U.S. Pat. No. 6,361,731 B1. These casting molds are transparent and have two separate filling openings. As a result, even high-viscosity bone cement paste can be introduced into the casting mold with little pressure, because the flow paths for the bone cement paste are relatively short. When using non-high-viscosity bone cement paste, the risk arises, once filling of the casting mold is complete, of bone cement paste flowing back out of the filling openings before curing begins.

In a further development, patent specifications U.S. Pat. No. 7,637,729 B2, U.S. Pat. No. 7,789,646 B2, U.S. Pat. No. 8,480,389 B2 and U.S. Pat. No. 8,801,983 B2 propose multipart casting molds for the production of modular hip spacers. These modular hip spacers consist of a spacer head and a separate stem. One casting mold is therefore needed for the spacer head and a separate casting mold for the stem. The casting mold for the stem is in one piece and has a thread at the filling opening for connecting the casting mold to a cement cartridge containing the bone cement paste.

US 2007/0222114 A1 describes a hip spacer mold. This spacer mold consists of a plurality of mold segments which are connected together. Thanks to the plurality of segments, the spacer mold may be adapted very precisely to the patient's anatomical circumstances. The spacer mold segments are joined together by means of worm drive hose clips. A PMMA bone cement paste (polymethyl methacrylate bone cement paste) is introduced through channels in the spacer mold. The complex structure of the casting mold makes it very complicated to join the spacer mold segments together and to remove the hip spacer once curing of the PMMA bone cement paste is complete.

WO 2009/073 781 A2 proposes a spacer mold for a hip spacer consisting of two parts which may be displaced relative to one another in order to enable adaptation of the length of the stem. A further casting mold is disclosed in EP 2 522 310 A1. This device consists of at least two parts, wherein in a first part there is arranged an insertion portion and in the second part an insertion receptacle. The two parts are able to be put into one another and form a casting mold for producing the stem of the hip spacer. EP 2 787 928 A1 describes a complex casting mold. This enables the production of hip spacers with different ball heads. The elements of the casting mold are fixed in place using connecting elements. U.S. Pat. No. 7,789,646 B2 describes a casting mold in which the filling opening of the casting mold can be closed using a plug once the bone cement paste has been introduced into the casting mold. Before that, however, the casting mold has to be unscrewed from the bone cement cartridge. When using non-high-viscosity bone cement paste, it is therefore possible, if the casting mold is held in an unfavorable way, for bone cement paste to run out during separation of the casting mold from the bone cement cartridge before the plug has been screwed or put in.

SUMMARY

The object of the present invention thus consists in overcoming the disadvantages of the prior art. In particular, the object of the invention consists in the development of an inexpensive device for producing a spacer by curing bone cement paste and in the development of a method which is able to be carried out simply and inexpensively for producing a spacer by curing bone cement paste, with which one-part spacers, in particular hip and shoulder spacers, can be produced by medical personnel in the operating room using bone cement paste, in particular polymethyl methacrylate-bone cement. Hip and shoulder spacers are of similar construction. They consist of a stem and a spacer head. A metal core may be or have been arranged inside the hip and shoulder spacer for the purpose of mechanical stabilization. It should be possible to produce spacers using not only low or non-high-viscosity but also high-viscosity (polymethyl methacrylate) bone cement paste A high injection pressure is needed for completely filling a casting mold with a high-viscosity bone cement paste. The casting mold of the device is intended to withstand this high injection pressure. The casting mold is therefore intended as far as possible withstand a pressure of 10 N/cm$^2$.

It is intended that the device be such that bone cement paste or fluid bone cement paste can be injected into a casting mold from a bone cement cartridge. When using a non-high-viscosity bone cement paste, it is intended for the bone cement paste not to flow out of the casting mold once it has been filled. To this end, it is necessary to configure the casting mold so as reliably to prevent non-high-viscosity bone cement paste from flowing out of the casting mold during separation of the casting mold from the cement cartridge. Such closure should be possible without the need for openings or valves of complex construction in the wall of the casting mold. Openings in the wall of the casting mold may lead to leaks in the casting mold if the bone cement paste is injected into the casting mold under high pressure. Furthermore, the sprue region of the casting mold should be configured such that, on the one hand, easy filling of the casting mold with bone cement paste is possible and, on the other hand, any sprue residues can be easily removed once curing of the bone cement paste is complete.

The objects of the invention are achieved by a device for producing a spacer by curing bone cement paste, wherein the spacer is provided in the medical field for temporarily replacing a joint or part of a joint comprising an articulating surface of the joint, in particular for temporarily replacing a hip joint or a shoulder joint, the device having A) a casting mold for molding the spacer from bone cement paste, the casting mold having at least one filling opening for introducing bone cement paste;

B) a valve seat, the valve seat being connected to the casting mold in the region of the at least one filling opening, wherein the valve seat has an in places or regionally closed head side with at least one first feed-through, wherein the at least one first feed-through opens into the at least one filling opening;

C) a valve body which is mounted so as to be rotatable relative to the valve seat and which has a sealing face, wherein the sealing face is oriented in the direction of the in places or regionally closed head side of the valve seat, wherein at least one second feed-through is arranged in the sealing face;

wherein the valve seat and the valve body together form a valve, wherein the valve is reversibly transferable into an open position and a closed position by rotation of the valve body relative to the valve seat, wherein, in the open position of the valve, the at least one first feed-through of the valve seat and the at least one second feed-through of the valve body are located above one another at least in places and provide a connection through the valve into the casting mold which is permeable to bone cement paste, wherein, in the closed position of the valve, the at least one first feed-through of the valve seat is covered by the sealing face of the valve body, wherein, in the closed position of the valve, the at least one filling opening of the casting mold is covered and closed for bone cement paste and wherein the valve is connected on the side remote from the casting mold to a port for liquid-tight connection of a bone cement cartridge or the valve has such a port.

Liquid-tight means that the non-cured, i.e. fluid, bone cement paste and preferably also a liquid monomer liquid as starting component of the bone cement cannot flow out of or penetrate through the connection at the port.

Covered for bone cement paste means that the bone cement paste in the valve is prevented from flowing to such a degree that it cannot flow through the valve prior to curing. For normal-viscosity bone cement pastes, it is sufficient to this end for the bone cement paste to be incapable of flowing in a straight line through the valve and for the free passage cross-sections to be smaller than 1 mm. Bone cement pastes are viscous or high-viscosity fluids, as indicated by the term "paste". The viscosity of a bone cement paste amounts to at least 10 Pa·s, which corresponds to the viscosity of liquid honey. In addition, the bone cement paste cures within a few minutes, meaning that passage is then no longer possible. Provision may preferably be made for the bone cement paste to have a viscosity of at least 10 Pa·s.

A bone cement paste or a fluid bone cement paste is understood to mean a mixed (i.e. ready-to-use) bone cement paste which has a high-viscosity consistency. The viscosity of bone cement preferably corresponds to that of honey or is even higher. The terms fluid bone cement and bone cement paste are used synonymously.

The casting mold is preferably internally hollow.

Provision may be made for the sealing face to be closed apart from the at least one second feed-through.

Provision may preferably also be made for the casting mold to have an interior which replicates a negative shape of a joint head, in particular of a hip joint head or a shoulder joint head.

Provision may also be made for the valve seat to be connected to a casting mold wall of the casting mold in liquid-impermeable manner.

Provision may further be made for the valve seat to be configured at one end face of a cavity delimited by the casting mold as a disk, in particular as a planar disk.

Provision may preferably also be made for the valve seat and the valve body to be hollow-cylindrical.

Provision may further be made for the casting mold to be in two parts or multiple parts, wherein the parts of the casting mold are preferably fastenable to one another in a liquid-tight manner by way of flanges. The casting mold is particularly preferably in two parts.

The casting mold is intended to withstand a pressure of 10 $N/cm^2$, in order also to enable the use of high-viscosity bone cement paste.

The terms "open state" and "closed state" of the valve or of the valve body relative to the valve seat and the terms "open position" and "closed position" of the valve or of the valve body relative to the valve seat are used synonymously.

In the present patent application, the statements of direction ("proximal", "distal" and "lateral") and the statements relating to planes ("sagittal plane", "front plane" and "transverse plane") relating to the spacer or the casting mold are used in the same way as would be understood as a main anatomical direction or body plane when inserted into the patient. For instance, "proximal" means towards the center of the body and "distal" means remote from the center of the body.

The stem is provided for connection to a bone (in the case of hip joint spacers to the femur) and for this purpose may preferably be introduced into a proximal end of the prepared bone or into the bone canal.

Provision may preferably be made for the device for producing a spacer, in particular a hip joint spacer or shoulder joint spacer, to be suitable for application of at least one antibiotic and/or antimycotic active ingredient.

The spacer should preferably be fabricated in one part from a biocompatible bone cement paste, such as polymethyl methacrylate (PMMA), wherein the PMMA particularly preferably contains at least one antibiotic and/or antimycotic dissolvable from the PMMA.

Provision may preferably be made for the regionally closed head side of the valve seat and the sealing face of the valve body to be disks or be disk-shaped.

Provision may preferably be made for the valve seat to delimit the filling opening of the casting mold.

Provision may be made for the valve seat to be connected to the casting mold so as not to be rotatable relative to the casting mold, preferably for the valve seat to be connected fixedly and/or rigidly to the casting mold.

In this way, sealing or connection of the valve seat for the bone cement paste relative to the casting mold may be achieved in a structurally simple and thus inexpensive way.

Provision may further be made for the valve to be manually operable, preferably manually operable from outside the device, wherein the valve body is particularly preferably manually rotatable relative to the valve seat and the valve is transferable by rotation from the closed position into the open position and from the open position into the closed position.

In this way, the valve of the device can conveniently be operated from outside, in order to change or detach a bone cement cartridge.

Provision may also be made for the valve to be operable by rotation or tilting of a cement cartridge connected to the port, wherein to this end the port is preferably arranged on the valve body.

Provision may moreover be made for the at least one first feed-through of the valve seat to be covered, in the closed position of the valve, with the sealing face of the valve body, wherein the regionally closed head side of the valve seat and the sealing face of the valve body are preferably spaced apart from one another by a maximum of 2 mm, particularly preferably by a maximum of 1 mm and very particularly preferably by a maximum of 0.5 mm.

In this way, it may be ensured that the bone cement paste filled into the casting mold (the fluid bone cement) cannot be expelled back out of the casting mold through the valve when the valve is closed. If the bone cement paste cures with these thicknesses or cross-sections in the region of the sprue, it may be readily manually broken off or cut through once the spacer has cured and need not be separated with a saw. Sprues of such thicknesses are harmless since they do not appreciably delay OP procedures during an OP.

Provision may also be made for the valve body to be mounted so as to be rotatable about an axis of rotation relative to the valve seat, wherein the axis of rotation extends perpendicular to the sealing face of the valve body or wherein the axis of rotation extends along an axis of rotational symmetry of the sealing face of the valve body.

As a result, the bone cement paste flowing through the valve can be cut or twisted off the valve body by rotation. This enables a smooth cut surface and little application of force during shearing. Rotation of the bone cement cartridge may further also be used for shearing the bone cement paste. It is preferred for the axis of rotation to extend along the axis of rotational symmetry of the sealing face of the valve body. If the axis of rotation extends perpendicular to the sealing face of the valve body, the valve may be constructed in the manner of a tap (for example for beer).

Provision may also be made for the valve body to be mounted so as to be rotatable about an axis of rotation relative to the valve seat, wherein the axis of rotation is oriented in the direction of the filling opening.

Provision may further be made for the valve body to be rotatable by an angle of a maximum of 280° relative to the valve seat, preferably of a maximum of 180°, particularly preferably of a maximum of 100° relative to the valve seat and very particularly preferably of up to 90° relative to the valve seat.

Two feed-throughs may preferably be arranged in each of the valve seat and the valve body, wherein two feed-throughs are preferably arranged offset by 180° about the center point of disks of the valve seat and of the valve body, wherein the disks form the regionally closed head side of the valve seat and the sealing face of the valve body.

Provision may further be made for the valve body to have a port for liquid-tight connection of a bone cement cartridge or to be firmly connected to such a port.

In this way, the valve body can be operated by means of a connected bone cement cartridge.

According to a preferred further development, provision may be made for the device to have an adapter element which is connected or connectable to a bone cement cartridge, wherein the adapter element is detachably and interlockingly connected or connectable to the port, such that an interior of the bone cement cartridge is connected or connectable permeably for bone cement paste via the adapter element to the at least one second feed-through.

This ensures that the bone cement paste can be straightforwardly filled into the casting mold from the bone cement cartridge through the valve in the open position thereof.

According to a further development of the present invention, provision may be made for the device to have a bone cement cartridge for mixing bone cement starting components and for delivering mixed bone cement paste from the bone cement cartridge and preferably to have a bone cement cartridge for mixing polymethyl methacrylate bone cement starting components and for delivering mixed polymethyl methacrylate bone cement paste from the bone cement cartridge, wherein the bone cement cartridge particularly preferably contains the bone cement starting components for producing the bone cement in mutually separate regions.

In this way, the device is further completed since the device may then also provide the bone cement paste which is filled into the casting mold for forming the spacer.

Provision may also be made for the casting mold to consist of a plastics film or substantially of a plastics film or for the casting mold to be constructed from two or more plastics films, which are welded or adhesively bonded together, and wherein the casting mold is preferably fabricated from PETG film and/or polyamide film and/or PE film.

In this way, the casting mold and thus the device can be inexpensively fabricated. The stated materials are suitable for shaping the spacer from the bone cement paste. In addition, the spacers can be readily removed from the mold after curing.

The term "plastics film" is understood to mean two-dimensional plastics with a film thickness of up to 2 mm. The plastics films of the casting molds may be produced by calendering or indeed by injection molding. Thermoforming and plastics injection molding are possible options for shaping the casting molds. The casting mold parts may be connected together by ultrasound welding, by high-frequency welding, thermal welding or by adhesive bonding. Combinations of joining methods are also possible. Alternatively, the parts of the casting mold may also be connected together mechanically, for example by clamping devices. PETG is a glycol-modified polyethylene terephthalate (PET), which is distinguished by its watery characteristics (viscosity) and is particularly suitable for injection molding.

Plastics films of PETG, polyamide and polyethylene (PE) with a film thickness of 500 μm to 2000 μm may be used for producing the casting molds. As a result, it is possible to produce casting molds which tolerate a pressure of 10 N/cm$^2$ for a period of a few minutes without splitting open.

Moreover, provision may be made for the sum of all openings of the at least one first feed-through in the closed head side to be at most as large as the closed surface of the head side and for the sum of all openings of the at least one second feed-through in the sealing face to be at most as large as the closed surface of the sealing face.

This ensures that the valve can be closed stably and impermeably to bone cement paste by rotation of the valve body relative to the valve seat.

Provision may further be made for the valve seat to have an inner thread on the inside and the valve body to have a matching outer thread on the outside, such that the valve body is able to be screwed into the valve seat.

Thanks to this measure, a good sealing effect can be achieved at the connection between the valve body and the valve seat. In addition, the valve can be simply and inexpensively assembled in this way.

Provision may also be made for the port to comprise, for liquid-tight connection of a bone cement cartridge, an inner thread in the valve body or an outer thread on the valve body, wherein an adapter element of the bone cement cartridge or on the bone cement cartridge preferably has a mating thread matching the inner thread or the outer thread.

In this way, a stable and liquid-tight connection to the port may on the one hand be produced and on the other hand use may be made of the rotation during the screwing movement at the start or after the end of the screwing movement to rotate the valve body relative to the valve seat and so transfer the valve from the open to the closed state or transfer the valve from the closed to the open state.

By using a suitable thread, an additional safety function of the device may in particular be achieved by its only being possible to detach the bone cement cartridge with the valve closed and its only being possible to open the valve with the bone cement cartridge connected.

Provision may be made for the inner thread in the valve body or the outer thread on the valve body to be a right-hand thread and for the valve to be transferable from the closed to the open position by equidirectional rightward rotation of the valve body and for the valve to be transferable from the open to the closed position by contradirectional leftward rotation of the valve body or for the inner thread in the valve body or the outer thread on the valve body to be a left-hand thread and for the valve to be transferable from the closed to the open position by equidirectional leftward rotation of the valve body and for the valve to be transferable from the open to the closed position by contradirectional rightward rotation of the valve body or for the inner thread of the valve seat and the inner thread and the outer thread of the valve body all to be left-hand threads or all to be right-hand threads, wherein an outer thread of an adapter element for liquid-tight connection of a bone cement cartridge to the port preferably also has the same direction of rotation.

The purpose of these measures is also to ensure that the valve closes automatically when the bone cement cartridge is unscrewed and the valve opens automatically when the bone cement cartridge is screwed in.

Provision may preferably also be made for the at least one first feed-through in the regionally closed head side to have the same size and shape as the at least one second feed-through in the sealing face.

Provision may preferably likewise be made for the at least one first feed-through in the regionally closed head side to be two first feed-throughs and the at least one second feed-through in the sealing face to be two second feed-throughs, wherein the two first feed-throughs are preferably arranged in the valve seat in quadrants arranged opposingly with regard to the axis of rotation of the valve body and the two second feed-throughs are arranged in the sealing face in quadrants arranged opposingly with regard to the axis of rotation of the valve body.

Thanks to these two measures, a sufficient flow area can be provided for the high-viscosity bone cement paste and unilateral loading of the valve which might otherwise lead to valve leaks can be avoided.

Provision may moreover also be made for a collar to be arranged on the sealing face of the valve body, which collar rests on an edge of the valve seat or a collar is arranged on the regionally closed head side of the valve seat, which collar rests on an edge of the valve body.

In this way, stable guidance of the valve body on the valve seat can be achieved. In the event of a given thread length of the valve body, the position of the at least one second feed-through may further be precisely defined with regard to the at least one first feed-through.

Provision may in this case be made for a radially oriented lever to be arranged on the circumferential surface of the valve body next to the collar.

Provision may further be made for a lever to be arranged on the valve body, which lever has a radial extent with regard to the axis of rotation of the valve body, wherein the lever preferably projects through an orifice in the casting mold or in the valve seat, wherein the orifice in the casting mold is optionally arranged in the region of the connection to the valve seat, wherein the orifice is dimensioned such that the valve may be transferred from the open position into the closed position and vice versa by rotation of the valve body in the valve seat by means of the lever, wherein the orifice is particularly preferably dimensioned such that the valve body may be rotated by a maximum of 90° relative to the valve seat.

As a result, the valve is conveniently manually operable from outside. Using this lever, the valve body can be rotated from the open position into the closed position of the valve.

According to a preferred further development, provision may be made for the valve body and the valve seat to be fabricated of plastics, in particular of thermoplastics, wherein the valve seat is preferably adhesively bonded or welded to a wall of the casting mold.

In this way, the valve and thus the device can be fabricated inexpensively and as a hygienic disposable product.

Provision may preferably be made for the valve seat to have ribs on its outside, which enter into or may enter into form-fitting connection with the casting mold.

Provision may also be made for the casting mold to have at least three or four cavities, starting from an inner chamber of the casting mold, for receiving retaining pins, wherein the casting mold is preferably in two parts and the cavities are preferably arranged in edges or flanges of at least one part of the two-part casting mold.

Using these cavities, a metal core may be arranged and precisely positioned in the spacer as reinforcement.

Provision may moreover be made for the device to have a metal core for arrangement in the casting mold, wherein the metal core preferably has bores for receiving retaining pins, wherein the bores are particularly preferably not arranged in a region of the casting mold for molding a sliding surface of the spacer, the bores very particularly preferably being arranged in a region of the casting mold for molding a stem of the spacer.

The stem of the spacer serves to provide connection to the bone and is covered with bone cement on implantation.

The metal core preferably consists of a biocompatible metal or of a biocompatible metal alloy, particularly preferably of surgical steel.

Provision may also be made for the device to have at least three or four retaining pins for retaining the metal core in the casting mold.

The metal core serves to stabilize the spacer and so ensure better usability of the treated joint.

The metal core is held by the retaining pins in a defined position within the casting mold. In this way, the thickness of the bone cement jacket around the metal core is defined. The retaining pins are preferably fabricated from a biocompatible plastics material. Polymethyl methacrylate is particularly suitable for this. Retaining pins of polymethyl methacrylate bond irreversibly to the bone cement paste. After curing of the bone cement paste, the retaining pins projecting out of the spacer are simply cut off. The residues of the retaining pins located inside the spacer remain therein.

Provision may also be made for at least one vent opening to be provided in the casting mold, through which air or gas can escape from the interior of the casting mold, wherein preferably at least one of the at least one vent opening, particularly preferably each of the at least one vent opening, is arranged in a region of the casting mold which forms a sliding surface or a joint head of the spacer.

In this way, air or gas can escape from the interior of the casting mold when the bone cement paste is introduced. Entrapped air and thus unevenness on the surface of the spacer may thereby avoided.

The objects underlying the present invention are also achieved by a method for producing a spacer for temporarily replacing a joint or part of a joint, in particular a hip joint or a shoulder joint, comprising an articulating surface of the joint, wherein the method is carried out with a device according to the invention, the method having the following chronological steps:
- A) connecting a bone cement cartridge to the port of the device in liquid-tight manner;
- B) injecting bone cement paste from the bone cement cartridge through the valve in the open position into the casting mold;
- C) rotating the valve body relative to the valve seat and so transferring the valve into the closed position and shearing off the bone cement paste at the at least one first feed-through in the regionally closed head side of the valve seat by rotating the valve body relative to the valve seat;
- D) detaching the bone cement cartridge from the port;
- E) curing the bone cement paste in the casting mold; and
- F) removing the resultant molded and cured spacer from the casting mold.

The spacer is intended for medical applications. The method according to the invention does not comprise implantation in a patient but merely the forming of the spacer. After step F), the spacer can be trimmed of flash, smoothed, sanded, cleaned, polished and/or roughened in places.

In order to remove the molded and cured spacer from the casting mold in step F), the casting mold can be opened after step E).

In the method according to the invention, provision may be made for the following intermediate steps to proceed after step D) and before step E):
- D2) connecting a new bone cement cartridge to the port of the device in liquid-tight manner, wherein bone cement paste or starting components for producing the bone cement paste is/are present in the new bone cement cartridge;
- D3) rotating the valve body relative to the valve seat and so transferring the valve into the open position;
- D4) injecting bone cement paste from the new bone cement cartridge through the valve in the open position into the casting mold;
- D5) rotating the valve body relative to the valve seat and so transferring the valve into the closed position and shearing off the bone cement paste at the at least one first feed-through in the regionally closed head side of the valve seat by rotating the valve body relative to the valve seat; and
- D6) detaching the new bone cement cartridge from the port;
- wherein steps D2) to D6) are preferably repeated once or multiple times with in each case new bone cement cartridges which contain bone cement paste or the starting components thereof until the casting mold is filled completely or as required with bone cement paste.

In this way, a casting mold with a large volume may be filled with a plurality of bone cement cartridges containing small volumes of the bone cement paste. This is advantageous, for example, for the production of large-volume hip joint spacers.

Provision may moreover be made for the bone cement paste to be mixed before step B), and preferably before step A), in the bone cement cartridge from a monomer liquid and a cement powder, wherein, optionally before step D3) and preferably before step D2), the bone cement paste is preferably mixed in the new bone cement cartridge from a monomer liquid and a cement powder.

In this way, a freshly mixed bone cement paste can be used for producing the spacer. PMMA bone cement pastes in particular can be stored for periods of more than a few minutes only with difficulty if at all in the mixed state. In addition, suitable therapeutic pharmaceutical active substances, such as antibiotics and antimycotics, may accordingly be mixed into the bone cement paste only shortly before production of the spacer.

Provision may further be made for the bone cement cartridge and/or the new bone cement cartridge to be rotated or screwed into the port for liquid-tight connection of the bone cement cartridge and/or the new bone cement cartridge to the port and, for detaching the bone cement cartridge and/or the new bone cement cartridge from the port, the bone cement cartridge or the new bone cement cartridge is rotated out of or unscrewed from the port.

In addition to being screw-fastened, the bone cement cartridge may for example be connected to the port with a bayonet closure.

By rotating or screwing the bone cement cartridge into the port, it is possible to provide a liquid-tight connection between the port and the bone cement cartridge. In addition, the rotation may also rotate or cause the valve body to rotate relative to the valve seat.

Provision may also be made for rotating the valve body relative to the valve seat to proceed by screwing the valve body in the valve seat or by manually rotating the valve body relative to the valve seat, wherein manual rotation preferably proceeds by operation of a lever extending radially away from the valve body and extending through an orifice in the casting mold or in the valve seat.

As a result, the valve is simply operable by the user.

Provision may also be made for injection of the bone cement paste from the bone cement cartridge or the new bone cement cartridge to proceed by pushing a piston into an interior of the bone cement cartridge.

In this way, the bone cement paste can straightforwardly be injected from the bone cement cartridge through the open valve into the casting mold.

Finally, provision may also be for a metal core to be arranged within the casting mold before step B) and preferably before step A), wherein the metal core is preferably spaced from an internal wall of the casting mold via a plurality of retaining pins, wherein the plurality of retaining pins are particularly preferably fastened in bores in the metal core and in cavities for receiving retaining pins in the internal wall of the casting mold.

In this way, with the assistance of the device, the spacer may be constructed with an internal reinforcement. The bone cement paste in this case flows around the metal core arranged in the casting mold.

The invention is based on the surprising recognition that, thanks to a valve body which is rotatable in a valve seat, it is possible to provide a device with a casting mold in which the sprue can be sheared off or largely sheared off with the valve body and simultaneously, in the event of ongoing pressure from a bone cement cartridge, to close the casting mold or at least constrict the remaining channels to such an extent that the bone cement paste can continue to be held under pressure in the casting mold so that it can be pressed against the inside of the casting mold, wherein the bone cement paste is simultaneously prevented from being expelled back out from the casting mold through the filling opening. The device also makes it possible to fill the casting mold in succession with the contents of a plurality of bone cement cartridges without the bone cement paste being able to flow back out of the casting mold through the filling opening. In this way, even with bone cement cartridges which provide only small volumes of bone cement, it is possible to produce spacers with a large volume.

Bone cement paste, in particular non-high-viscosity bone cement paste, cannot flow out of the casting mold through the closure or closed valve. Any formation of defects in the spacer as a result of bone cement flowing out is prevented as a result. Furthermore, the measures according to the invention ensure that the residue of bone cement paste left behind in the bone cement cartridge is separated from the bone cement paste in the casting mold. Once curing of the bone cement paste is complete, it is therefore no longer necessary to separate the sprue mechanically, for example by sawing. Any remaining thin connections can easily be broken or cut off. This saves time and effort for the OP personnel.

The sprue of the spacer is formed by the filling opening with the valve seat and the valve body. Rotating the valve body relative to the valve seat from the open position into the closed position of the valve closes the casting mold impermeably to bone cement paste. This means that the sprue formed by the valve seat and the valve body, or the sprue-shaping parts simultaneously function as a valve. There is no need for complex additional valves.

The valve body may be manually rotated relative to the valve seat by a lever on the outside of the valve body. Rotation may advantageously also proceed by the valve body being co-rotated by the bone cement cartridge when the bone cement cartridge is unscrewed. It is, however, necessary here for a limit stop to limit the rotational movement of the valve body relative to the valve seat so that closure can be reliable and so that the valve body cannot be completely rotated out of the valve seat.

A spacer produced with the device may advantageously be used in the context of two-stage septic revisions, in which an infection with two or more microbial microorganisms and in particular with problematic microorganisms is present.

An exemplary device according to the invention may be composed of
   a) a bone cement cartridge for mixing polymethyl methacrylate-bone cement components and for delivering mixed polymethyl methacrylate bone cement paste,
   b) an adapter element, which is connected or connectable to the cartridge head of the bone cement cartridge, wherein the adapter element may form a reversible interlocking connection and wherein the adapter element has a feed-through which liquid-permeably connects the interior of the cement cartridge to the surroundings,
   c) a hollow casting mold made from plastics film, which has a filling opening for introduction of the bone cement paste,
   d) a dimensionally stable hollow-cylindrical valve seat,
   d1) which is arranged non-rotatably in the filling opening of the casting mold for introduction of the bone cement paste,
   d2) wherein the dimensionally stable valve seat is connected liquid-impermeably to the casting mold wall,
   d3) wherein at the end face, which delimits the cavity of the casting mold, the dimensionally stable valve seat is configured as a disk which has at least one first feed-through which liquid-permeably connects the interior of the casting mold to the surroundings, wherein the area of the at least one first feed-through only occupies a maximum of 50 percent of the disk area of the valve seat, and d4) wherein the valve seat has an inner thread on the inside, e) a dimensionally stable, hollow-cylindrical valve body, e1) which has an outer thread on the outside of the hollow cylinder, which thread is able to be screwed together with the inner thread of the dimensionally stable valve seat, e2) wherein an inner thread or parts of an inner thread, which is or are reversibly connectable to the adapter element by screwing, are arranged on the inside of the hollow cylinder of the valve body, e3) wherein the valve body has at one end face, which faces the cavity of the casting mold and takes the form of a disk, the at least one second feed-through, wherein the area of the at least one second feed-through only occupies a maximum of 50 percent of the disk area of the valve body, and e4) wherein the at least one second feed-through has an approximately identical size and shape as the at least one first feed-through of the dimensionally stable valve seat, and f) wherein, after being screwed into the dimensionally stable valve seat, the valve body is rotated in an open position in such a way that the at least one second feed-through is located above the at least one first feed-through and a liquid-permeable connection from the interior of the casting mold to the surroundings or the bone cement cartridge is produced and can be rotated into a closed position such that the at least one second feed-through does not overlap with or cover the at least one first feed-through.

Once injection of the bone cement paste into the cavity of the casting mold is complete, the valve body is rotated manually such that the at least one second feed-through of the valve body is no longer located above or aligned with the at least one first feed-through of the dimensionally stable valve seat. In this way, the cavity of the casting mold is liquid-impermeably closed. Even a non-high-viscosity bone cement paste is consequently unable to flow out of the casting mold.

An exemplary method according to the invention for producing spacers with the device according to the invention may comprise the following successive steps:

a) providing the casting mold, b) mixing the bone cement powder with the monomer liquid in a bone cement cartridge until a bone cement paste has formed, wherein the bone cement cartridge has an adapter element on the cartridge head which is liquid-permeably connected to the interior of the cartridge, c) liquid-permeably connecting the bone cement cartridge to the casting mold by screwing the adapter element into an inner thread of the valve body, d) injecting the bone cement paste from the bone cement cartridge into the casting mold with the assistance of an expression device, wherein the bone cement paste expels the air in the cavity of the casting mold and the expelled air preferably emerges from the cavity of the casting mold into the surroundings through at least one vent opening, e) rotating the bone cement cartridge with the adapter element out of the valve body, wherein the valve body is rotated from the open position into the closed position of the valve, whereby the at least one first feed-through and the at least one second feed-through are no longer located above one another, such that no bone cement paste can emerge from the cavity of the casting mold into the surroundings through the valve, f) detaching the bone cement cartridge from the casting mold, g) curing the bone cement paste in the casting mold, h) opening the casting mold once the bone cement paste is cured and i) removing the spacer.

An alternative exemplary method according to the invention for producing spacers with the device according to the invention may comprise the following successive steps:

a) providing the casting mold, b) mixing the bone cement powder with the monomer liquid in a bone cement cartridge until a bone cement paste has formed, wherein the bone cement cartridge has an adapter element on the cartridge head which is liquid-permeably connected to the interior of the cartridge, c) liquid-permeably connecting the bone cement cartridge to the casting mold by screwing the adapter element into an inner thread of the valve body, d) injecting the bone cement paste from the bone cement cartridge into the casting mold with the assistance of an expression device, wherein the bone cement paste expels the air in the cavity of the casting mold and the expelled air preferably emerges from the cavity of the casting mold into the surroundings through at least one vent opening, e) manually rotating a lever on the valve body contrary to the direction of rotation of the thread of the valve body, wherein the valve body is rotated from the open position into the closed position of the valve, whereby the at least one first feed-through and the at least one second feed-through are no longer located above one another, such that no bone cement paste can emerge from the cavity of the casting mold into the surroundings through the valve, f) rotating the bone cement cartridge with the adapter element out of the valve body, g) detaching the bone cement cartridge from the casting mold, h) curing the bone cement paste in the casting mold, i) opening the casting mold once the bone cement paste is cured and j) removing the spacer.

BRIEF DESCRIPTION OF THE DRAWINGS

Further exemplary embodiments of the invention are explained below with reference to twenty-eight schematic figures but without thereby limiting the invention. In the figures.

DETAILED DESCRIPTION

FIGS. 1 to 10 are drawings showing various views of a first exemplary embodiment of a device according to the invention for producing a hip joint spacer and parts thereof.

Figure 1:
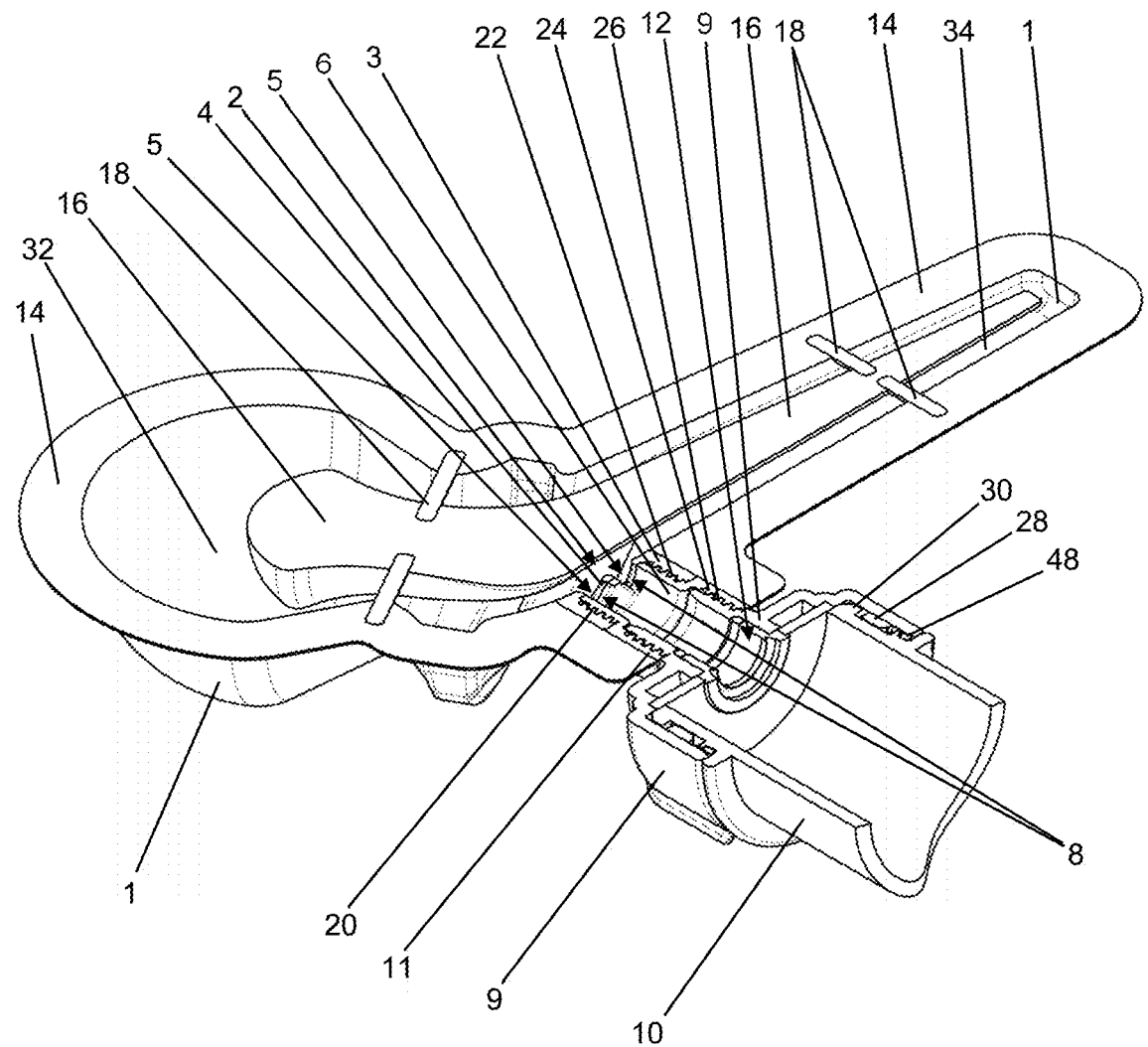
FIG. 1 shows a schematic perspective cross-sectional view of a first exemplary device according to the invention for producing a hip joint spacer with the valve open.
Figure 2:
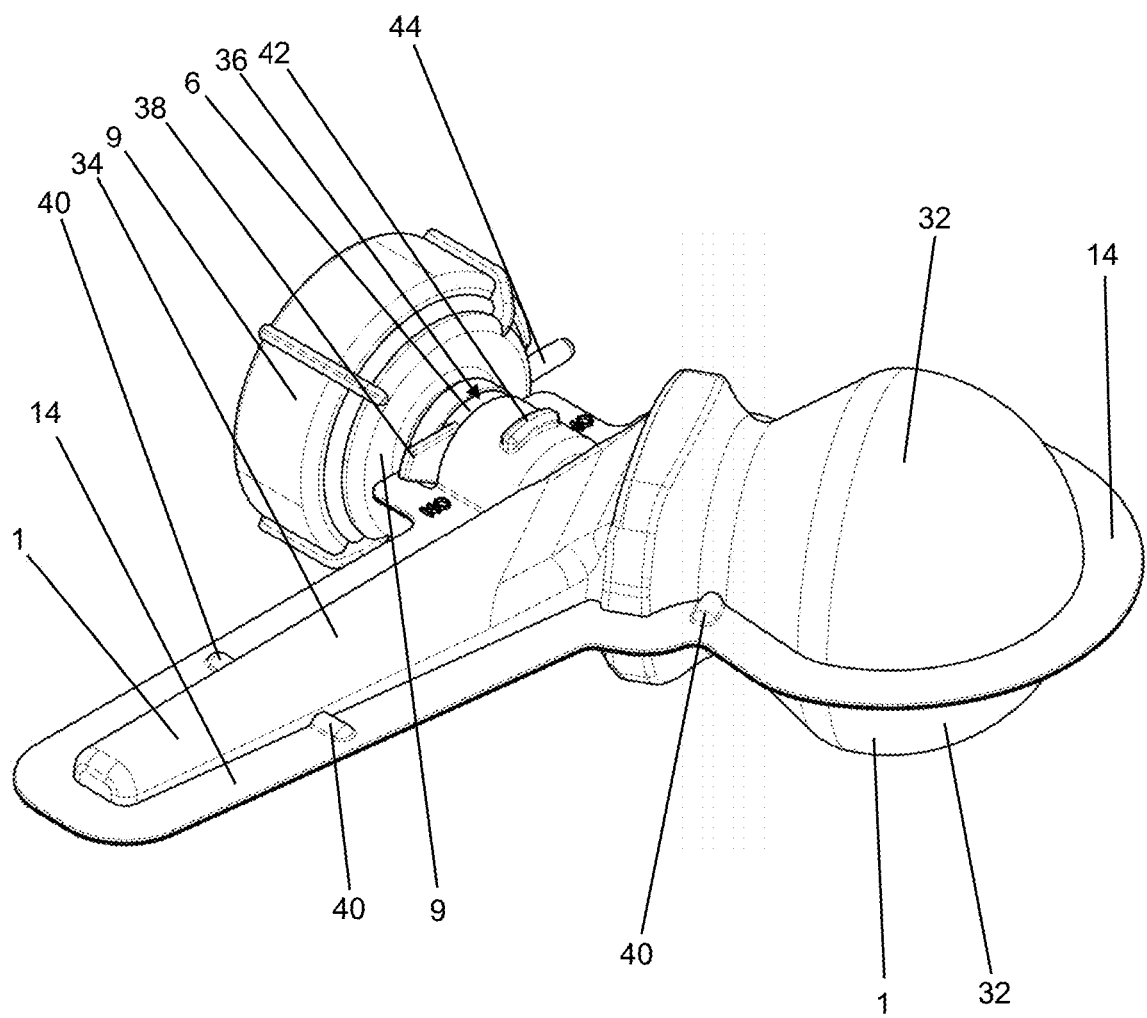
FIG. 2 shows a schematic perspective external view of the first device according to the invention according to FIG. 1.
Figure 3:
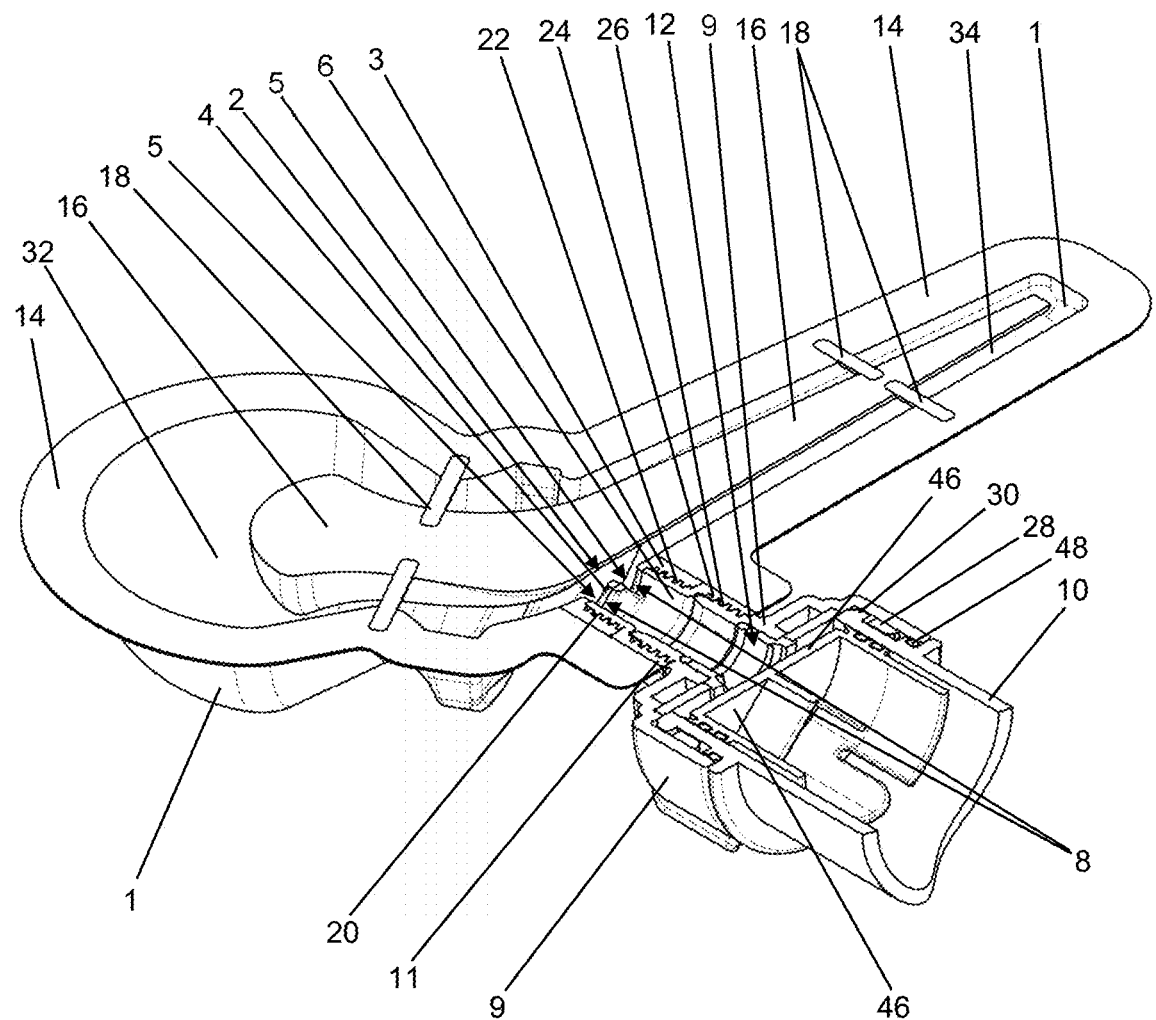
FIG. 3 shows a schematic perspective cross-sectional view of the first device according to the invention according to FIGS. 1 and 2 with the valve open.
Figure 6:
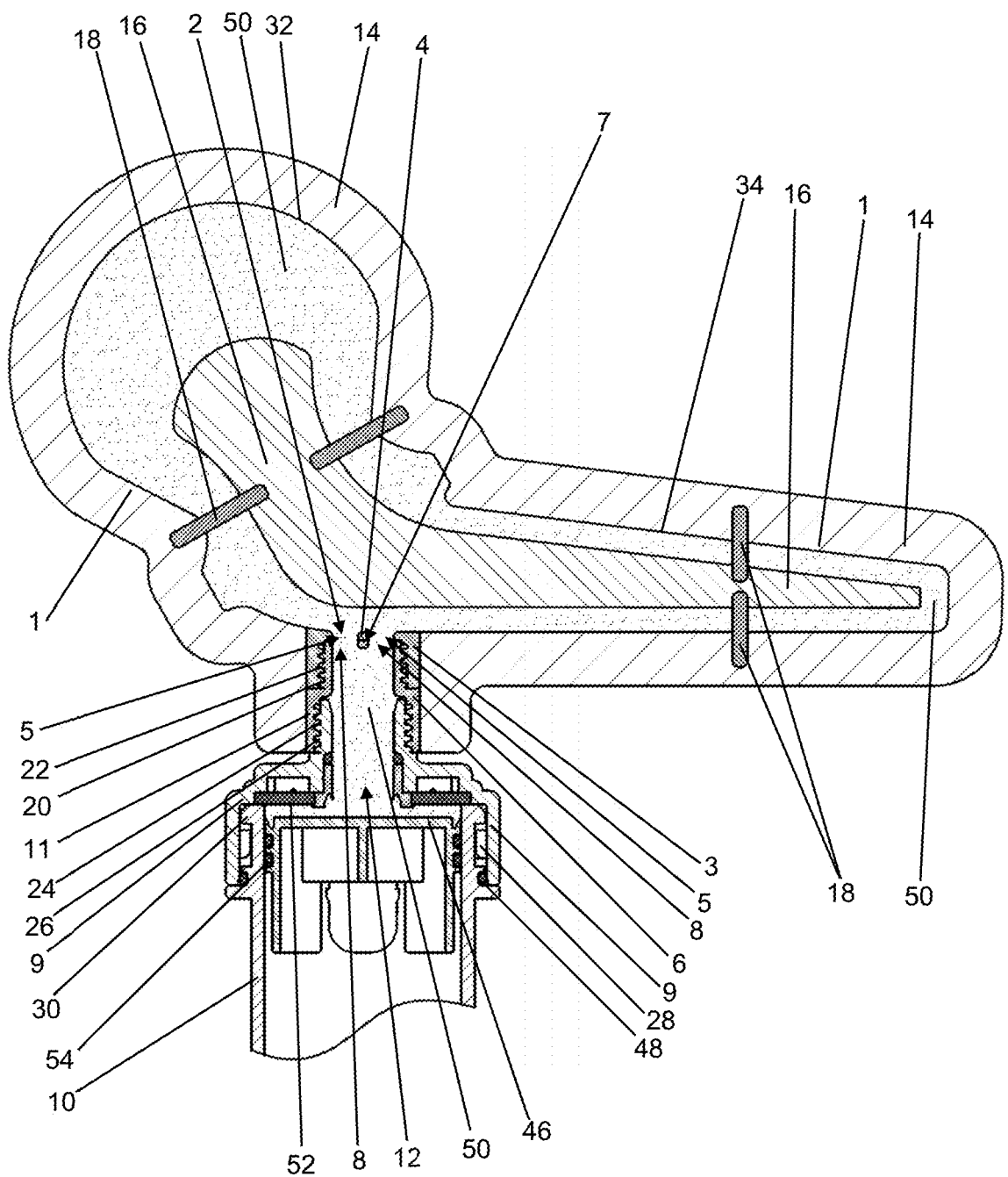
FIG. 6 shows a schematic cross-sectional view of the first device according to the invention with a casting mold filled with bone cement paste.
Figure 7:
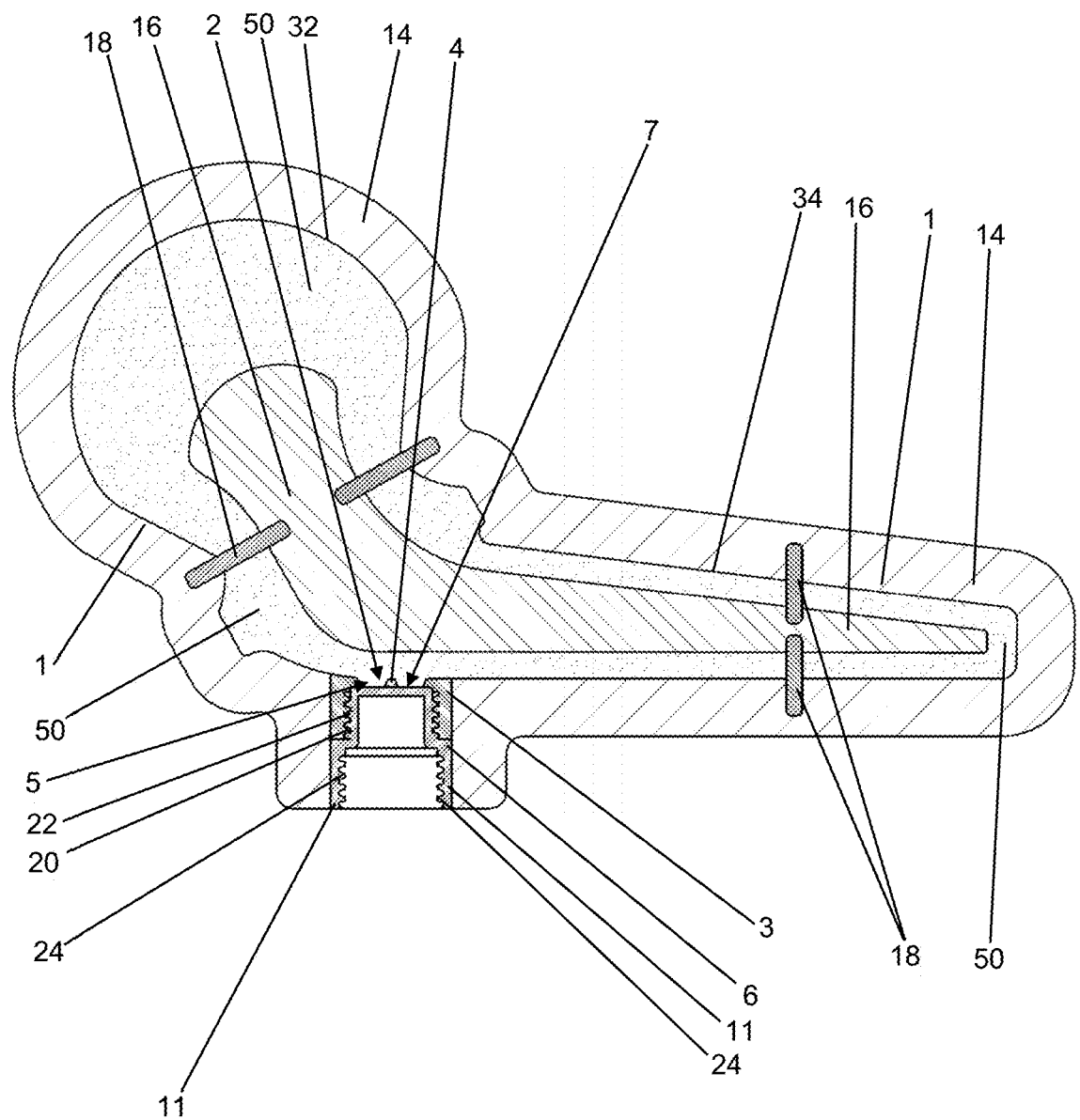
FIG. 7 shows a schematic cross-sectional view of the first device according to the invention with the valve closed after removal of a bone cement cartridge and an adapter element from the casting mold.
Figure 8:
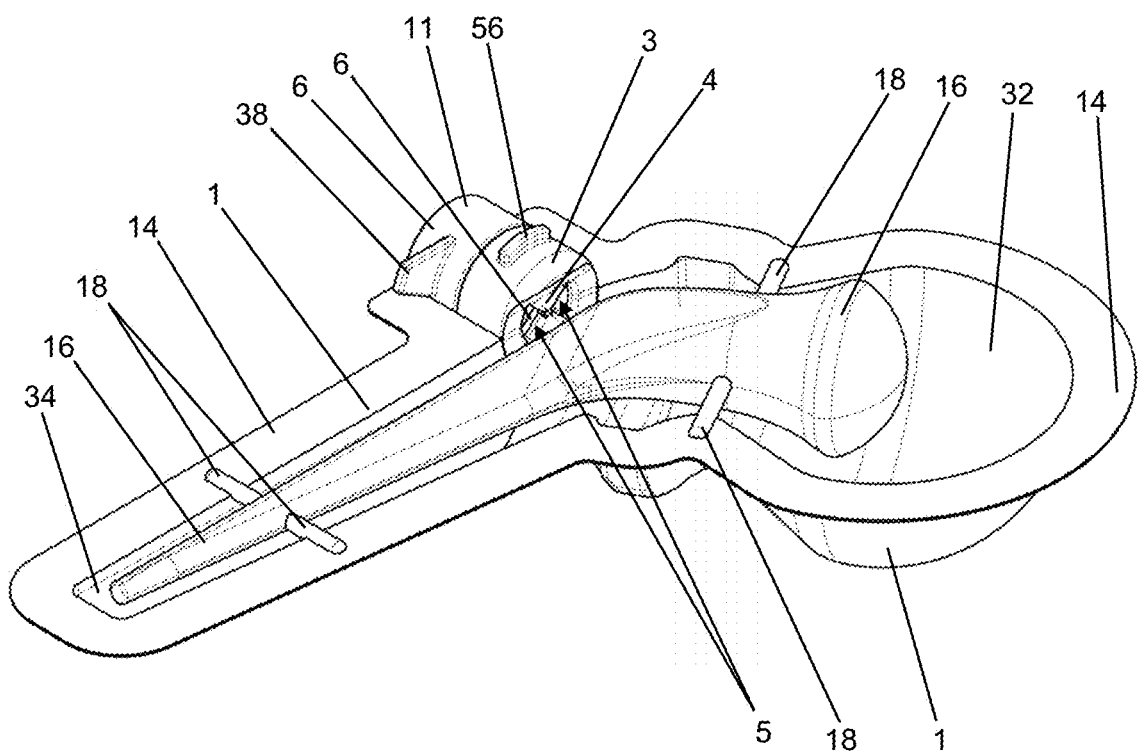
FIG. 8 shows a schematic perspective view of the open first device according to the invention with the valve open without the second part of the casting mold but with inserted metal core.
Figure 9:
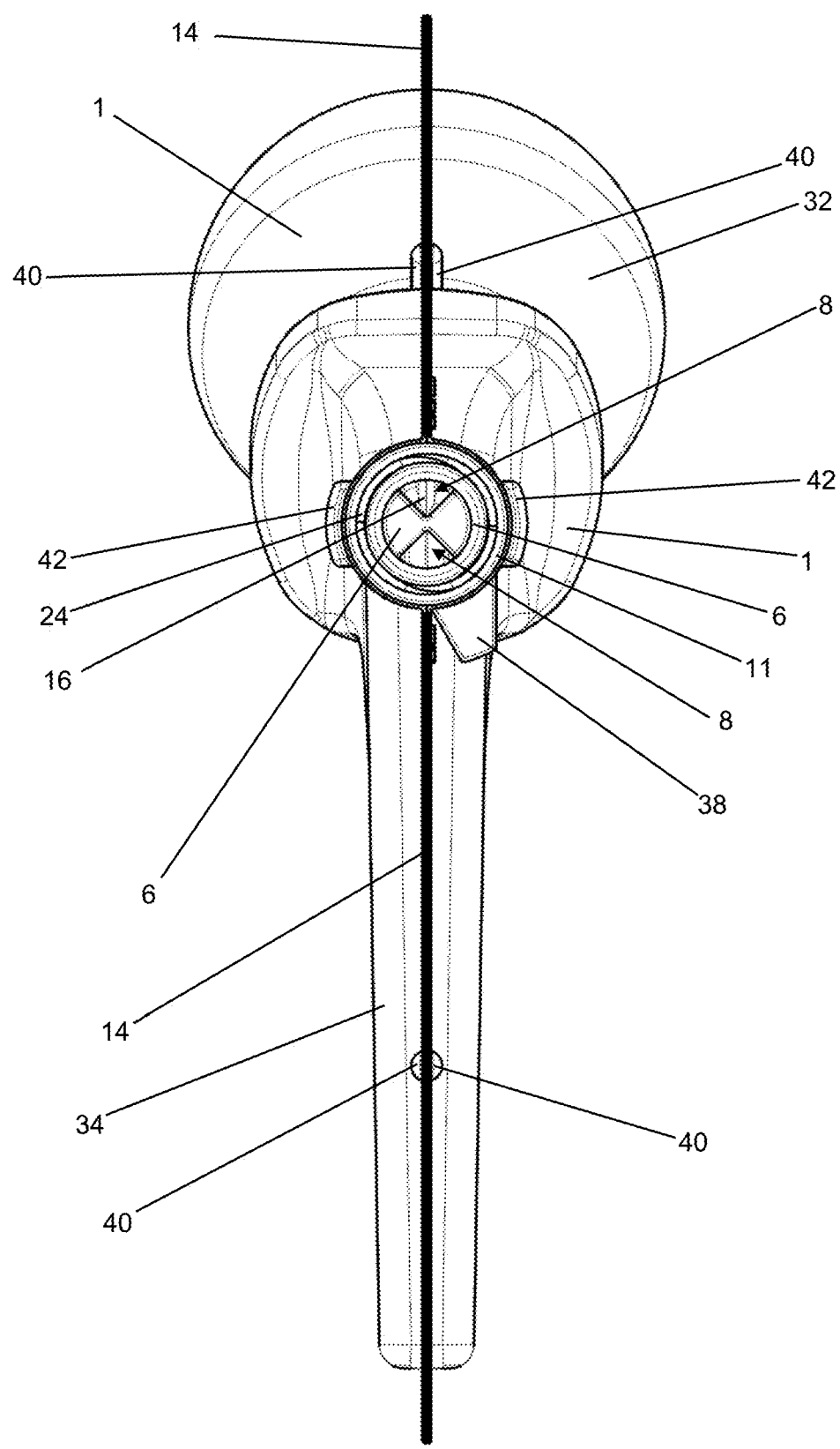
FIG. 9 shows a schematic perspective external view of one side with the port of the first device according to the invention with the valve open.
Figure 10:
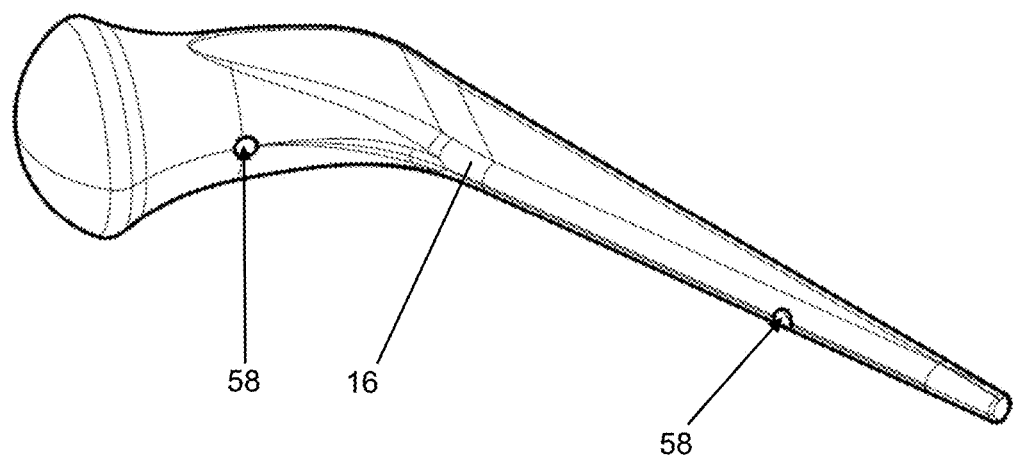
FIG. 10 shows a schematic perspective view of a metal core for a device according to the invention according to FIGS. 1 to 9.
Figure 11:
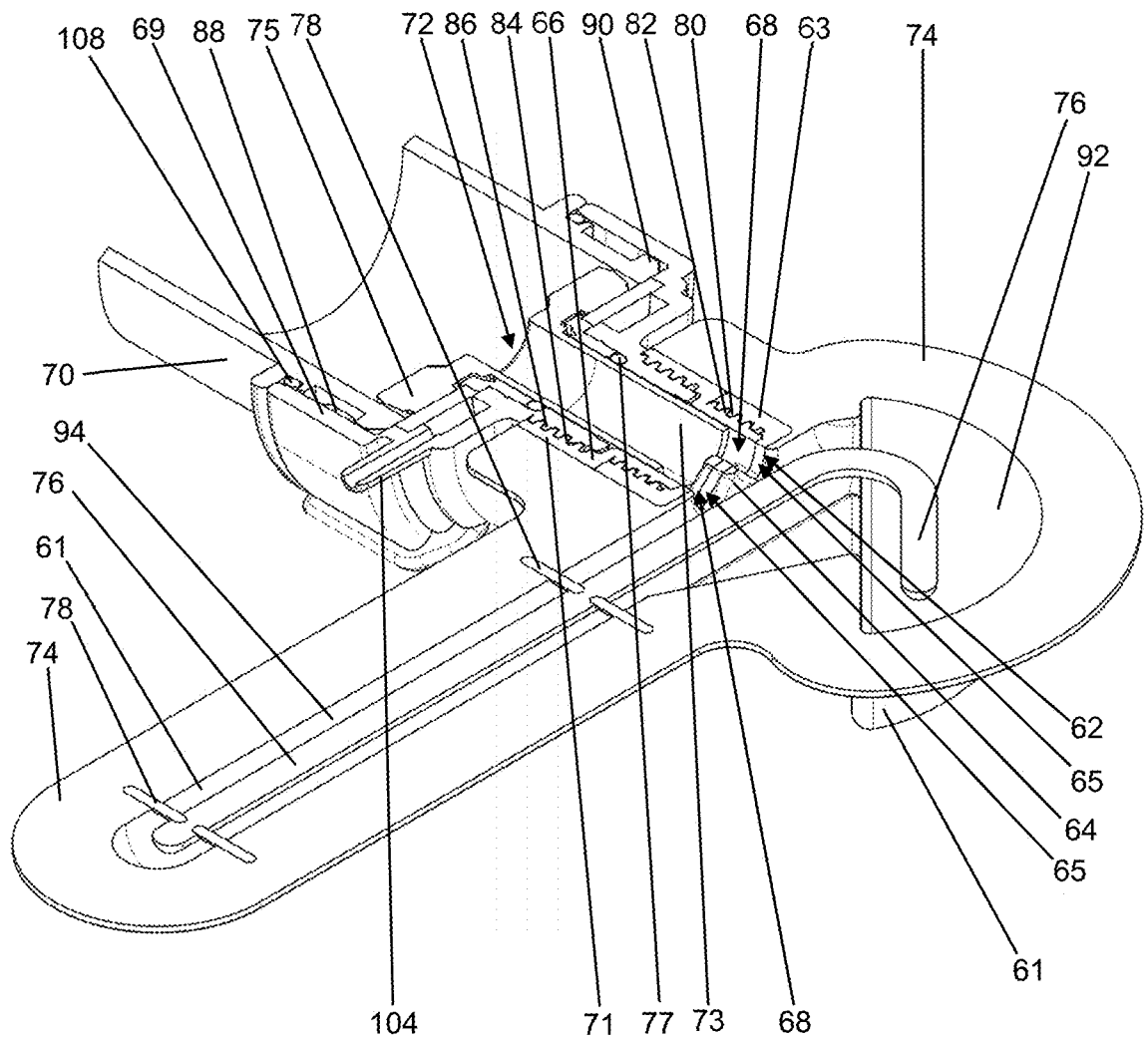
FIG. 11 shows a schematic perspective cross-sectional view of a second exemplary device according to the invention for producing a shoulder joint spacer with the valve open.

The first device according to the invention is suitable and provided for producing a spacer for a hip joint. The device comprises a casting mold 1. The casting mold 1 may be constructed in two parts. FIGS. 1 and 3 to 8 in each case show just one of the two parts of the casting mold 1. FIGS. 2 and 9 show both parts of the casting mold 1. A filling opening 2 for the introduction of bone cement paste 50 may be formed on one side of the casting mold 1, which filling opening may be defined in each case in both parts of the casting mold 1 by a semicircular cylindrical opening. A valve seat 3 may be arranged in this filling opening 2. The valve seat 3 may be firmly connected to a part of the casting mold 1, as shown in FIG. 8. For better and tighter connection of the valve seat 3 to the casting mold 1, the valve seat 3 may have patterning on its external surface, for example longitudinal grooves, which are arranged parallel to the cylinder axis of a cylindrical outer wall of the valve seat 3.

The valve seat 3 may take the form of a hollow cylinder which, apart from two first feed-throughs 5, is closed on a head side 4 oriented in the direction of the filling opening 2. The two first feed-throughs 5 may be quadrant-shaped and may preferably be arranged rotated or offset relative to one another by 180° with regard to the cylinder axis of the valve seat 3. A valve body 6 may be arranged in the interior of the valve seat 3 so as to be axially rotatable relative to the valve seat 3. The valve body 6 may have a sealing face 7 or surface oriented in the direction of the head side 4 of the valve seat 3. The valve body 6 may be constructed as a stepped hollow cylinder, the front part of which can be screwed or put into the valve seat 3.

Two second feed-throughs 8 may be arranged in the sealing face 7. The two second feed-throughs 8 may, similarly to the first feed-throughs 5, be quadrant-shaped and may preferably be arranged rotated relative to one another by 180° with regard to the cylinder axis of the valve body 6. The valve seat 3 and valve body 6 together form a valve of the device. An adapter element 9 for liquid-tight connection of a bone cement cartridge 10 may be screwed into the valve body 6. The bone cement cartridge 10 and the adapter element 9 may be part of the device according to the invention. The valve body 6 may on its open side, which is remote from the sealing face 7, be formed as a port 11 for connecting the adapter element 9.

The bone cement cartridge 10 may have on its front side a delivery opening 12 for delivering the bone cement paste 50 from the bone cement cartridge 10. The delivery opening 12 may be arranged in and delimited by the adapter element 9. The adapter element 9 may close the bone cement cartridge 10 on its front side apart from the delivery opening 12 and optionally apart from a vacuum port 44.

The casting mold 1 can be inexpensively fabricated from plastics film. The plastics film may have a plurality of layers. The two parts of the casting mold 1 may be fastened together via flanges 14. By connecting the two parts of the casting mold 1 via the flanges 14, the casting mold 1 may be closed to the outside. Vent openings (not visible in FIGS. 1 to 9) may be arranged in the casting mold 1. Air or gas can escape through the vent openings from the interior of the closed casting mold 1 when a bone cement paste 50 is filled into the casting mold 1 through the filling opening 2.

A metal core 16 may be placed in the interior of the casting mold 1. The metal core 16 may consist of surgical steel or of titanium. Alternatively, it would theoretically also be possible to fabricate the metal core 16 from a plastics material such as PMMA. The metal core 16 may be connected to the casting mold 1 via retaining pins 18. The metal core 16 may be spaced from the internal wall of the casting mold 1 with the aid of the retaining pins 18, such that the bone cement paste 50 can flow right around the metal core 16. The metal core 16 brings about stabilization of the spacer. The retaining pins 18 may consist of PMMA. This can irreversibly bond to a bone cement paste 50 of PMMA.

The valve seat 3 may have an inner thread 20 on its inside. On the front half of the valve body 6 facing the sealing face 7, the valve body 6 may have on the outside thereof an outer thread 22 matching the inner thread 20 of the valve seat 3. The valve body 6 may be screwed with its outer thread 22 into the inner thread 20 of the valve seat 3.

The first feed-throughs 5 and the second feed-throughs 8 may be brought into overlap with one another by screwing the valve body 6 into the valve seat 3 until the limit stop is reached. The valve is then in the open state. In this open state, a bone cement paste 50 may flow through the first feed-throughs 5 and through the second feed-throughs 8 out of the bone cement cartridge 10 into the casting mold 1. By making a quarter rotation (by 90°) of the valve body 6 relative to the valve seat 3, i.e. by unscrewing the valve body 6 from the valve seat 3, the first feed-throughs 5 and the second feed-throughs 8 may be offset relative to one another, such that the sealing face 7 of the valve body 6 covers the first feed-throughs 5 of the valve seat 3 and the closed regions of the head side 4 of the valve seat 3 cover the second feed-throughs 8 of the valve body 6. The valve is then in the closed state. Due to the small stroke of the valve body 6 relative to the valve seat 3 in the event of a quarter rotation, the gap arising between the valve body 6 and the valve seat 3 is so narrow (less than 1 mm wide) that a bone cement paste 50 of a normal, let alone high, viscosity, is incapable of passing through the gap. This is particularly the case because the bone cement paste 50 is deflected from its actual direction of flow by 90° in the gap.

The reverse side of the valve body 6 may have an inner thread 24 arranged in the port 11. The front side of the adapter element 9 has on its front side an outer thread 26 which matches the inner thread 24. The adapter element 9 may accordingly be screwed into the port 11 of the valve body 6. In this way, a liquid-tight connection can be created between the bone cement cartridge 10 and the valve body 6 and thus into the casting mold 1. The inner thread 20 of the valve seat 3, the outer thread 22 of the valve body 6, the inner thread 24 of the valve body 6 and the outer thread 26 of the adapter element 9 may all have the same direction of rotation, i.e. all these threads are right-hand threads or left-hand threads. As a result, the valve can be opened by screwing the adapter element 9 into the port 11 and continuing to rotate the adapter element 9 in the same direction. At the same time, the valve body 6 also provides a seal relative to the valve seat 3.

The adapter element 9 may be or have been connected via a latching means 28 on the adapter element 9 to a mating latch 30 on a cylindrical wall of the bone cement cartridge 10. A circumferential seal 48 which seals the cylindrical wall of the bone cement cartridge 10 relative to the adapter element 9 may be provided for sealing.

The casting mold 1 may have a joint head molding 32 for forming a joint head of a spacer and a stem molding 34 for forming a stem of a spacer. Moreover, an orifice 36 for lever 38 of the valve body 6 may be arranged in the casting mold 1 in the region of the filling opening 2. The lever 38 may be connected to the valve body 6. The valve body 6 can be rotated in the valve seat 3 with the lever 38. The orifice 36 is preferably precisely large enough for the valve body 6 to be rotatable only by a maximum of a quarter rotation relative to the valve seat 3. As a result, with the assistance of the lever 38, the valve can be transferred manually from outside from the open state into the closed state or from the closed state into the open state.

In the region of the flanges 14, shapes 40 may be arranged in the casting mold 1 for cavities, in which shapes the retaining pins 18 may be arranged. Shapes 42 for valve fastening may further be arranged in the casting mold 1 in the walls delimiting the filling opening 2, which shapes are provided for receiving matching projections 56 (see FIG. 8) on the cylindrical outside of the valve seat 3. Through engagement of the projections 56 in the shapes 42 for valve fastening, the valve seat 3 cannot be rotated in the filling opening 2 and a stable connection is provided.

A vacuum port 44 which is capable of evacuating an interior of the bone cement cartridge 10 in which the bone cement paste 50 is mixed may be arranged in the adapter element 9. As a result, the bone cement paste 50 can be mixed under a vacuum.

A piston 46 for discharging the bone cement paste 50 from the bone cement cartridge 10 through the valve into the casting mold 1 may be arranged in the cylindrical interior of the bone cement cartridge 10. The piston 46 may to this end be cylindrically shaped on the outside and be sealed relative to the cylindrical interior by means of two circumferential seals 54. By advancing the piston 46, the bone cement paste 50 can be pressed out of the delivery opening 12 of the bone cement cartridge 10 into or through the open valve.

A porous disk 52 may be arranged in the adapter element 9. The porous disk 52 is impermeable to the bone cement paste 50 and its starting components. The vacuum port 44 can be covered by the porous disk 52. This prevents any bone cement powder as a starting component of the bone cement paste 50 from being able to penetrate into the vacuum port 44.

The course of a method according to the invention is shown in FIGS. 4 to 7 with reference to the first device according to the invention. First of all, the metal core 16 may be positioned with the retaining pins 18 in the casting mold 1. To this end, the retaining pins 18 may be arranged and retained at one end between the two parts of the casting mold 1 in the cavities formed by the shapes 40 and arranged with the other end in matching bores 58 in the metal core 16. The casting mold 1 may then be closed.

Figure 4:
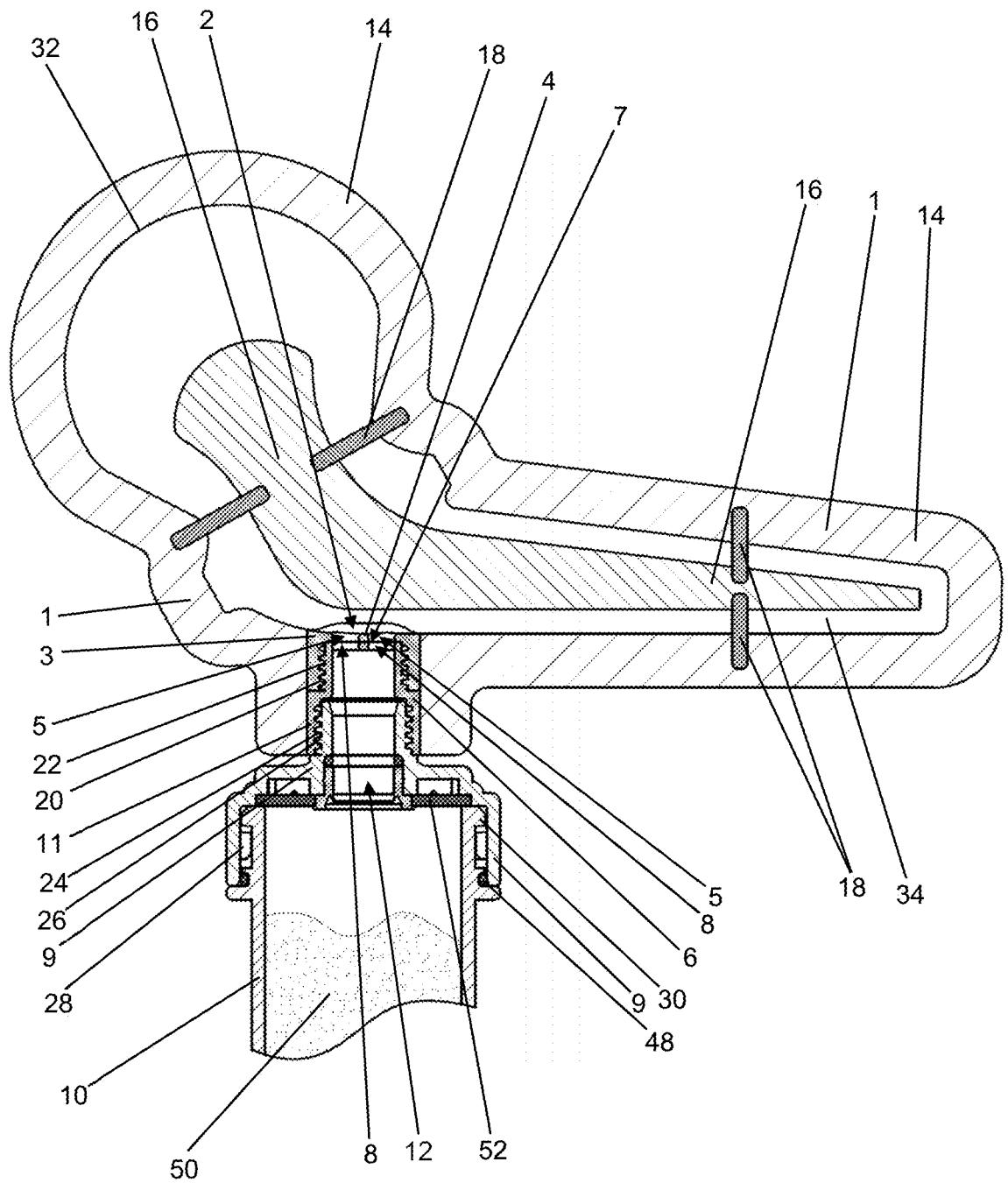
FIG. 4 shows a schematic cross-sectional view of the first device according to the invention with the valve open prior to the filling of bone cement paste into a casting mold of the device.

A bone cement paste 50 can be mixed under a vacuum in the bone cement cartridge 10. The bone cement cartridge 10 can then be screwed with the adapter element 9 into the port 11 of the valve body 6. On screwing in the adapter element 9, the valve can be transferred into the open position by screwing the valve body 6 into the valve seat 3 until the limit stop is reached. FIG. 4 shows this situation.

Figure 5:
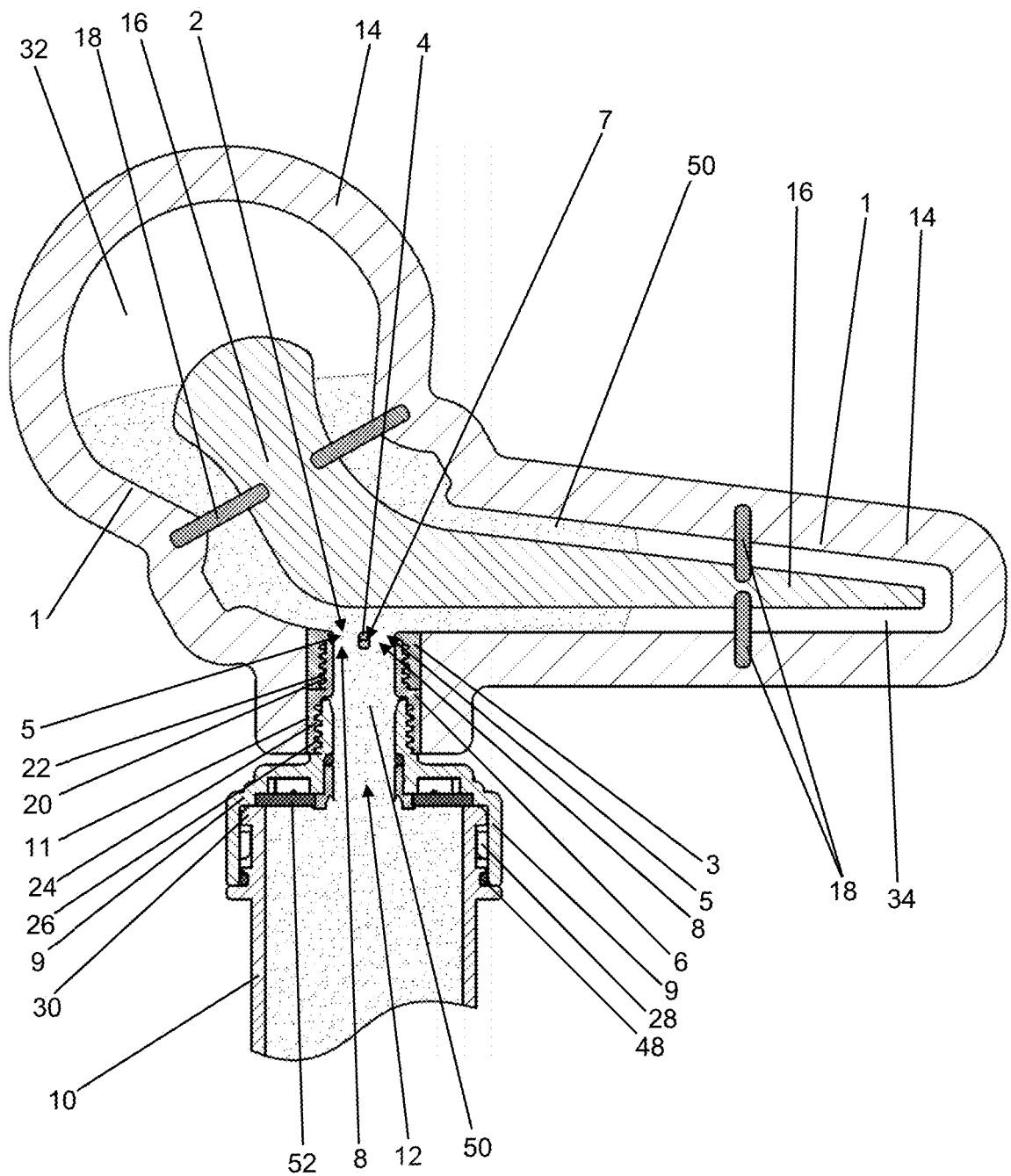
FIG. 5 shows a schematic cross-sectional view of the first device according to the invention during the filling of bone cement paste into the casting mold.

The bone cement paste 50 is then pressed out of the bone cement cartridge 10 through the valve and through the overlapping first feed-throughs 5 and second feed-throughs 8 into the casting mold 1 by advancing the piston 46. FIG. 5 shows this situation. By closing the valve by manually operating the lever 38 and so rotating the valve body 6 by a quarter rotation relative to the valve seat 3, a new bone cement cartridge 10 can be attached at intervals if the volume of the bone cement paste 50 from a single bone cement cartridge 10 is not enough to fill the casting mold 1 completely. The bone cement paste 50 contained in the casting mold 1 cannot flow back out again since the first passages 5 and the second passages 8 are covered in the closed position of the valve and the gap therebetween is insufficient for the viscous bone cement paste 50 to be able flow through.

At some point, the casting mold 1 is filled with the bone cement paste 50. FIG. 6 shows this situation. Air or gas has escaped from the casting mold 1 through vent openings in the casting mold 1. By closing the valve with the lever 38, the bone cement paste 50 is sheared or cut off. The bone cement cartridge 10 can be unscrewed and removed. Any remaining thin connections simply tear or break away. FIG. 7 shows this situation.

In this state, the bone cement paste 50 can be cured in the casting mold 1. Then, the spacer formed in this way is removed from the casting mold 1. The projecting retaining pins 18 may be cut off. Any sprue caused by the valve seat 3 and the first passages 5 can likewise be cut off and removed. Points caused by the vent openings may also be removed. The surface of the spacer can be polished and/or coated, for example with antibiotics.

Instead of a casting mold 1 for molding a hip joint spacer, it is also straightforwardly possible to use a casting mold for molding a different spacer.

Figure 18:
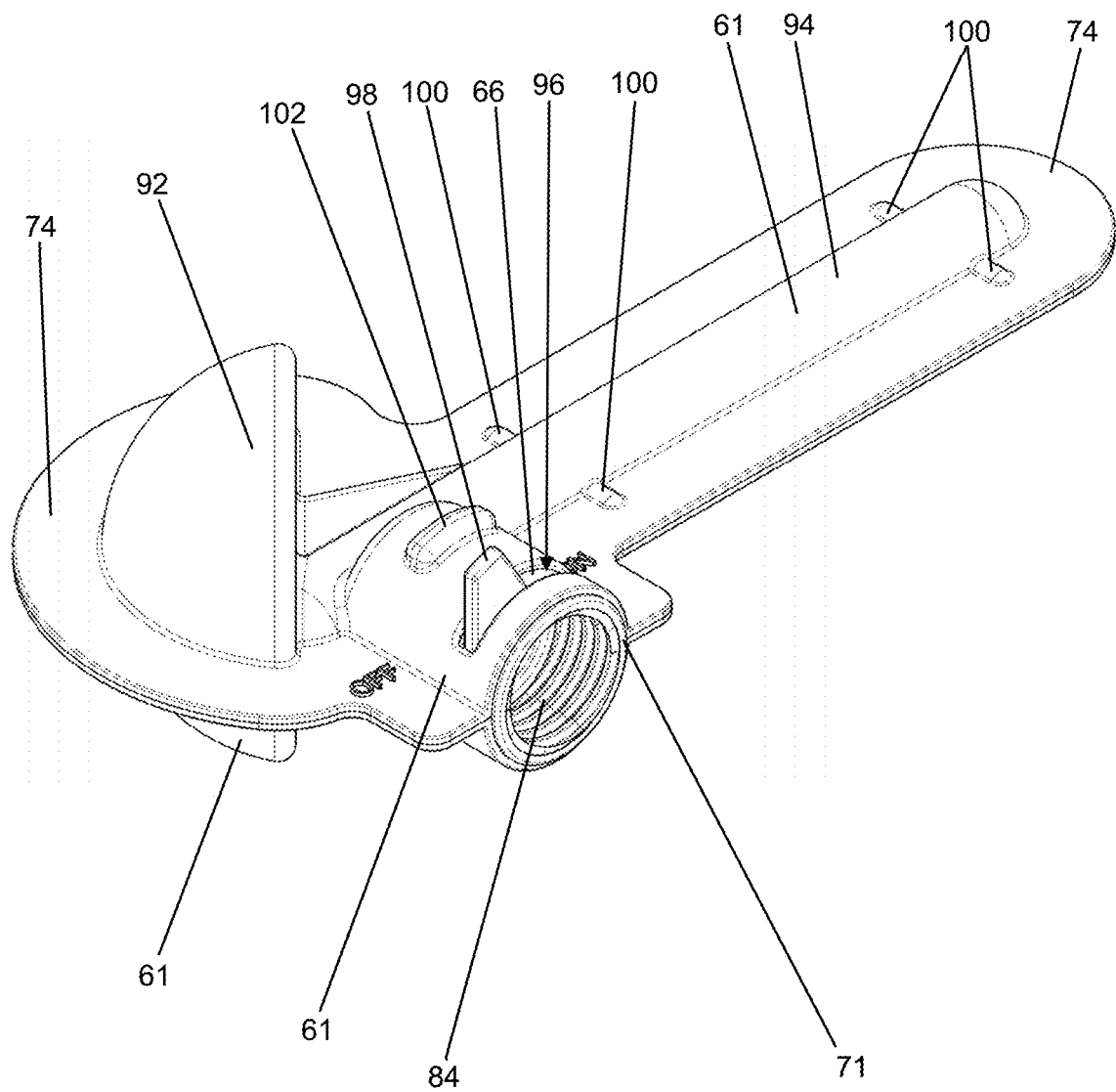
FIG. 18 shows a schematic perspective external view of the closed second device according to the invention according to FIGS. 11 to 17 with the valve closed.
Figure 19:
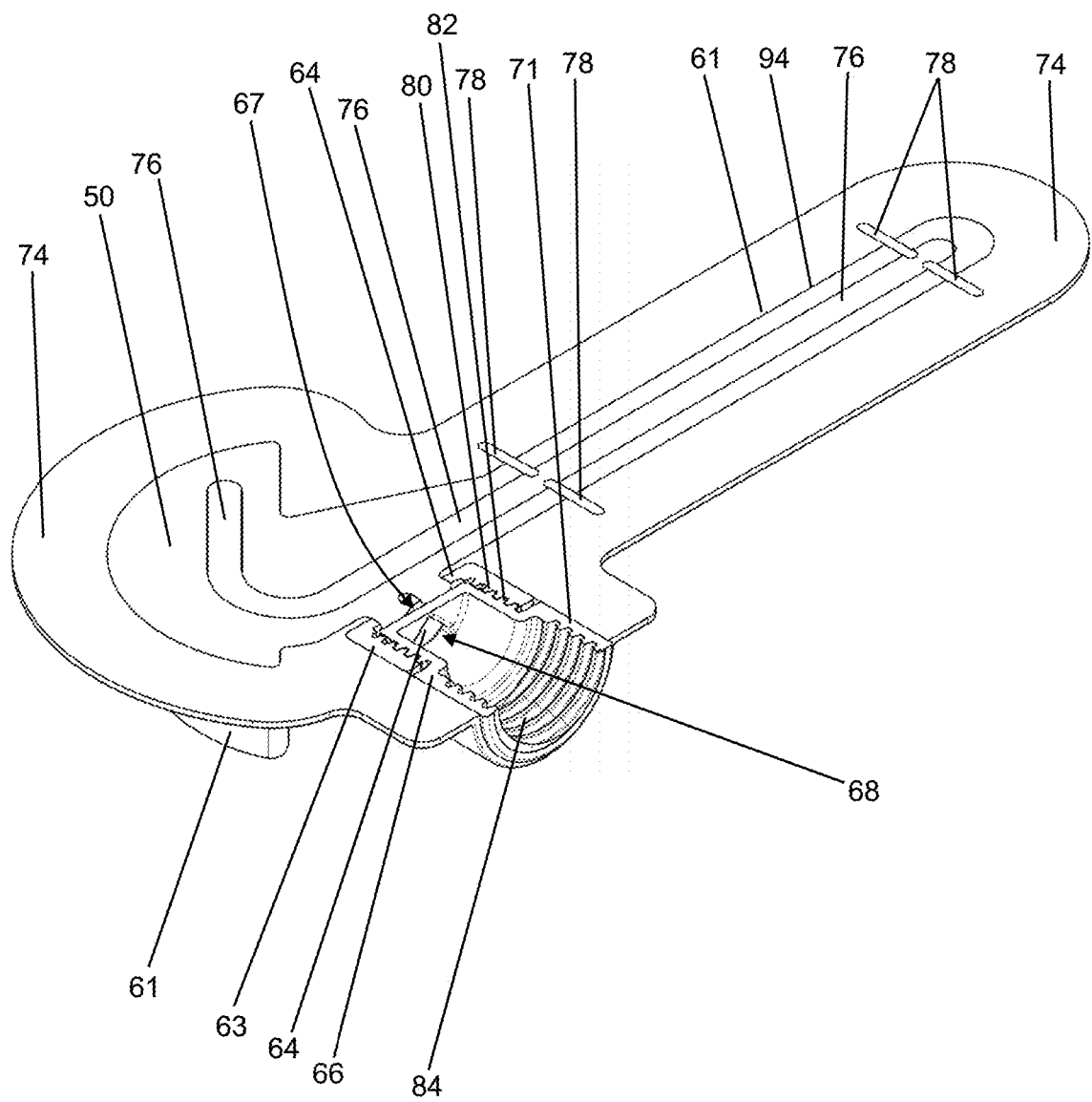
FIG. 19 shows a schematic perspective cross-sectional view of the second device according to the invention with the valve closed after the introduction of bone cement paste.
Figure 20:
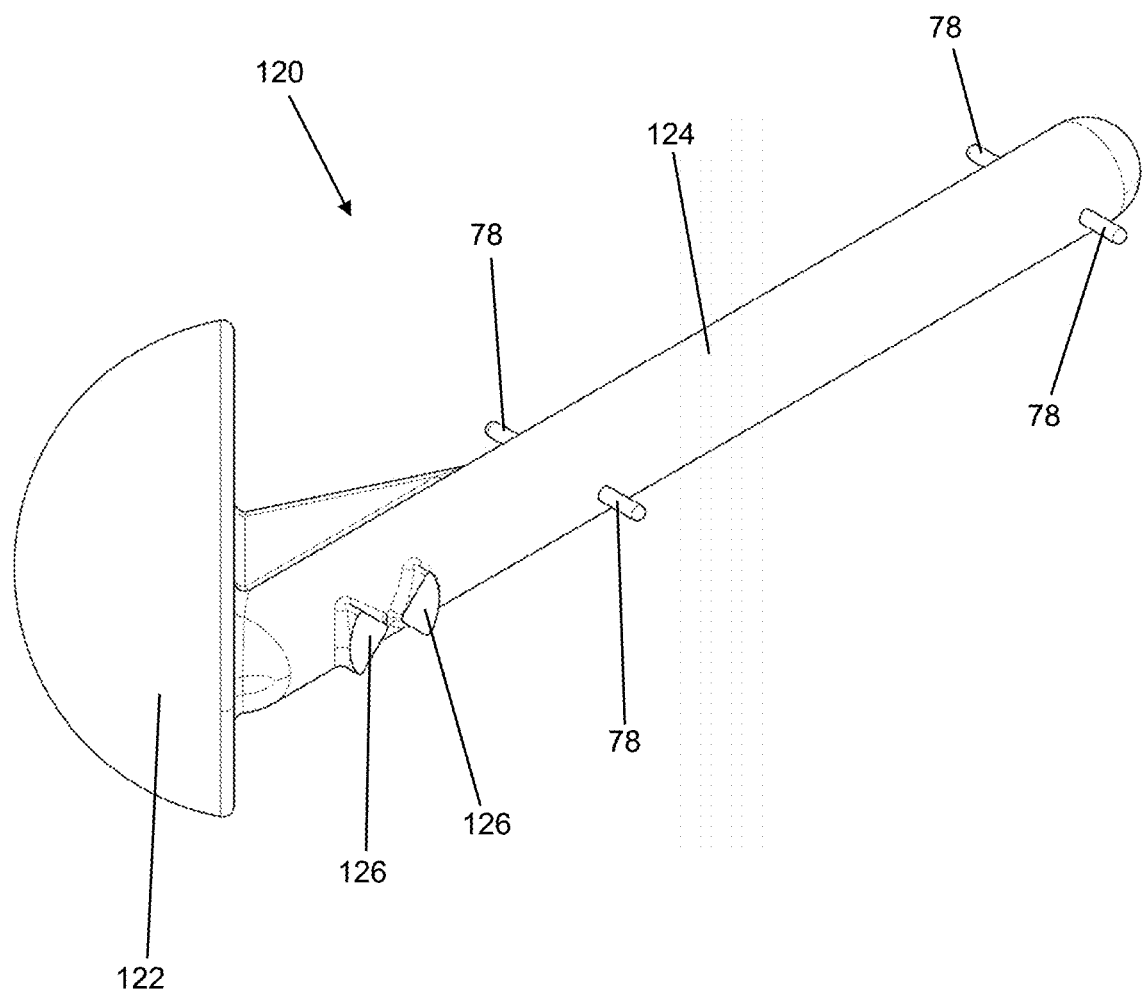
FIG. 20 shows a perspective view of a spacer which has been produced using a second device according to the invention according to FIGS. 11 to 19.
Figure 21:
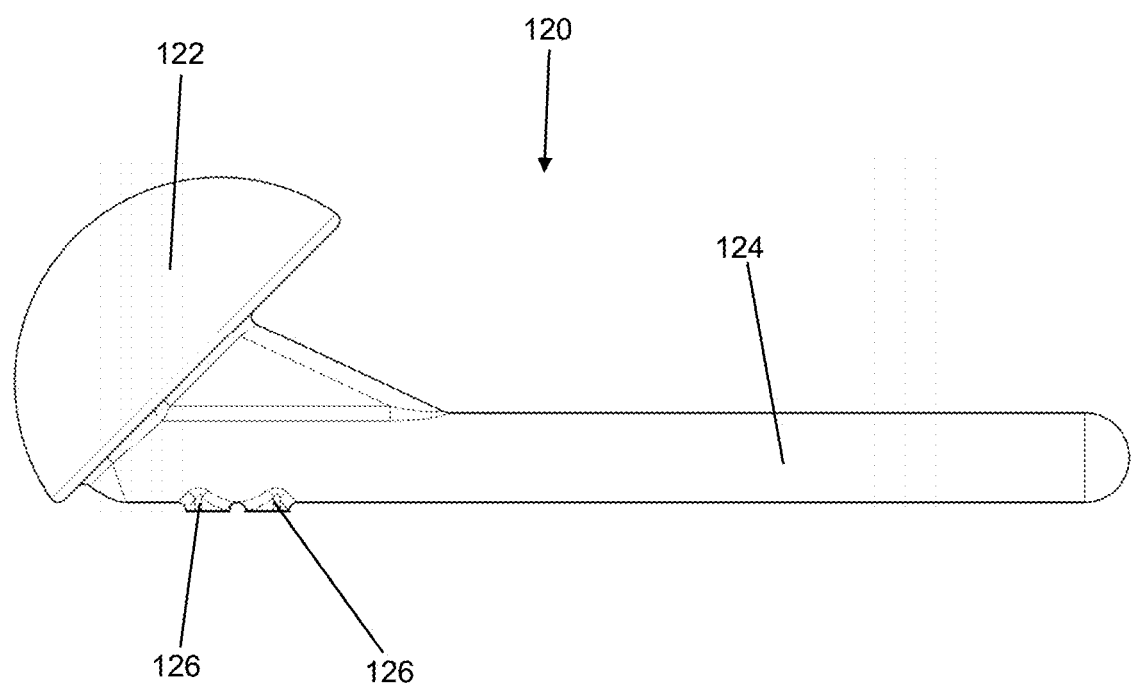
FIG. 21 shows a side view of the spacer according to FIG. 20, in which projecting retaining pins have been removed.
Figure 22:
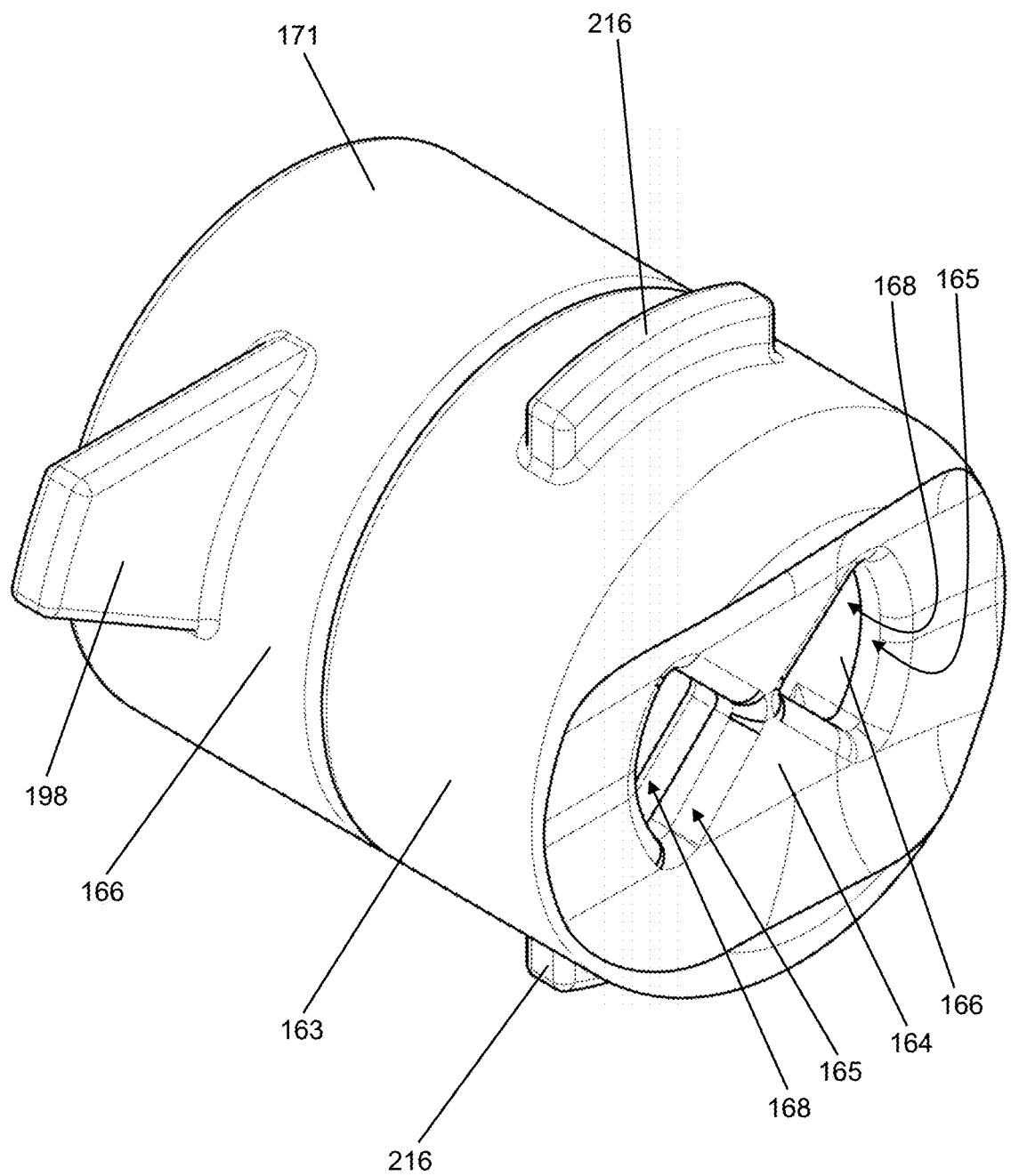
FIG. 22 shows a schematic perspective view of a valve for a device according to the invention in the open state.
Figure 23:
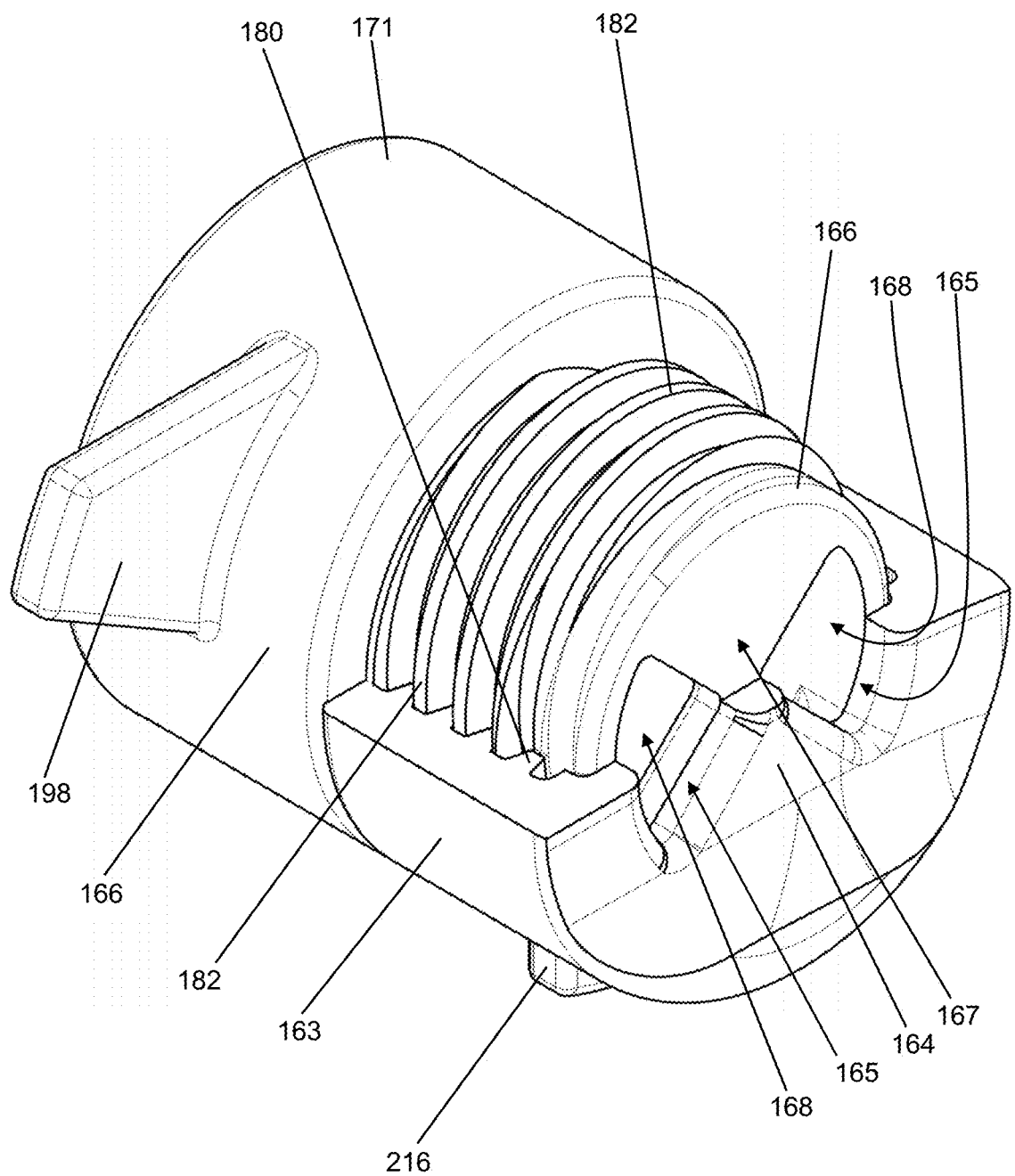
FIG. 23 shows a schematic perspective partial cross-sectional view of the valve according to FIG. 22 in the open state.
Figure 24:
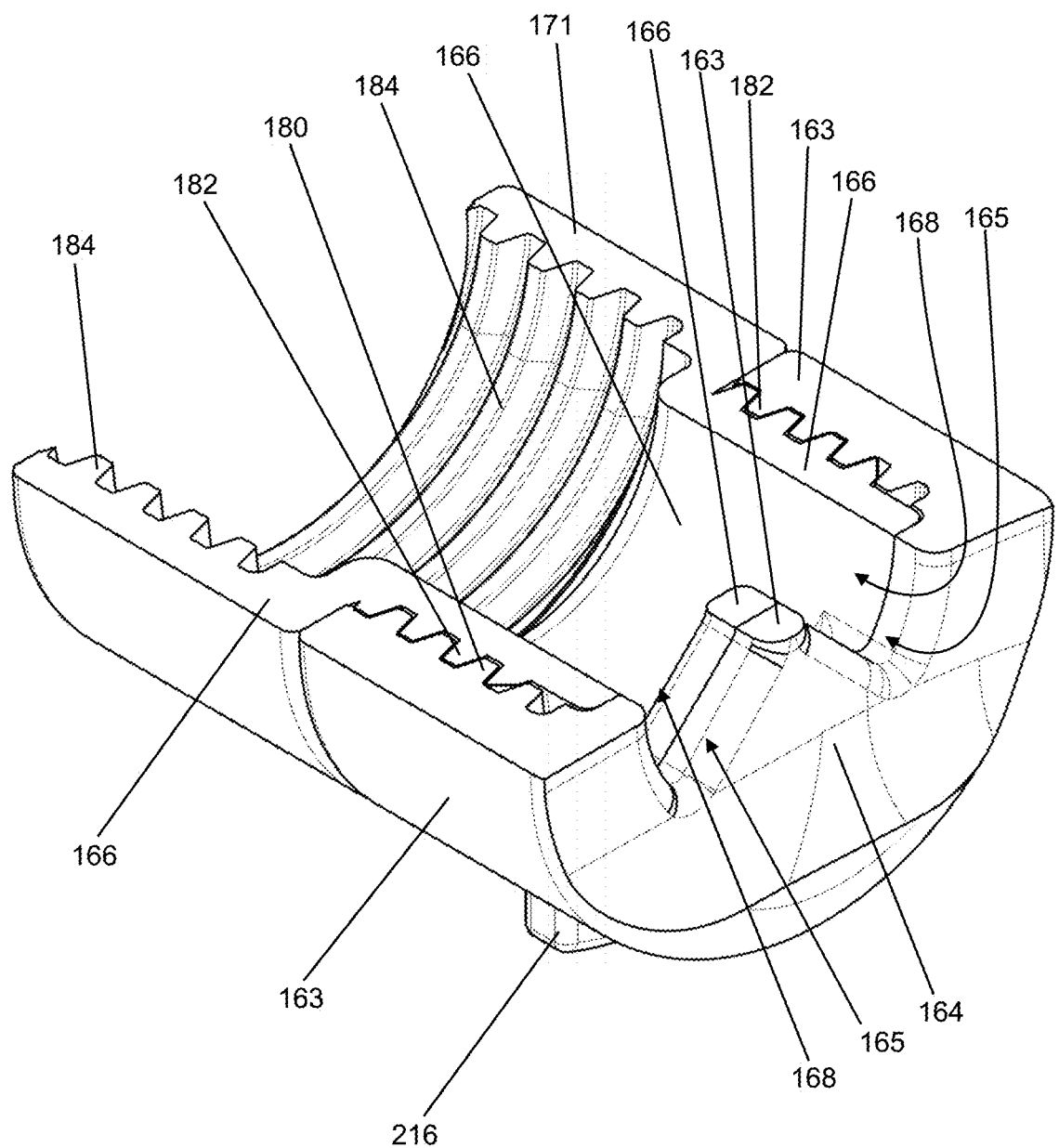
FIG. 24 shows a schematic perspective cross-sectional view through the valve according to FIGS. 22 and 23 in the open state.
Figure 25:
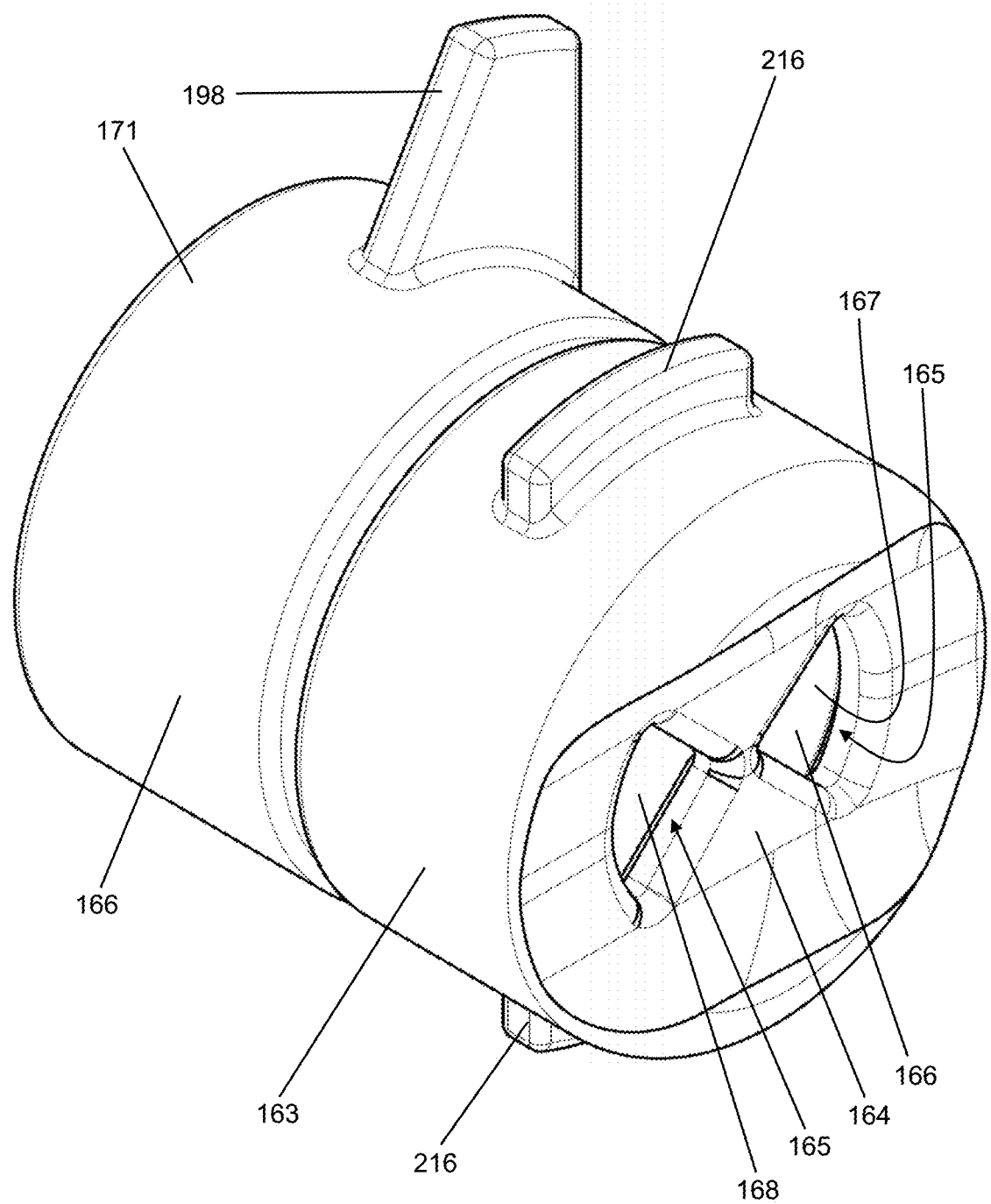
FIG. 25 shows a schematic perspective view of the valve according to FIGS. 22 to 24 in the closed state.
Figure 26:
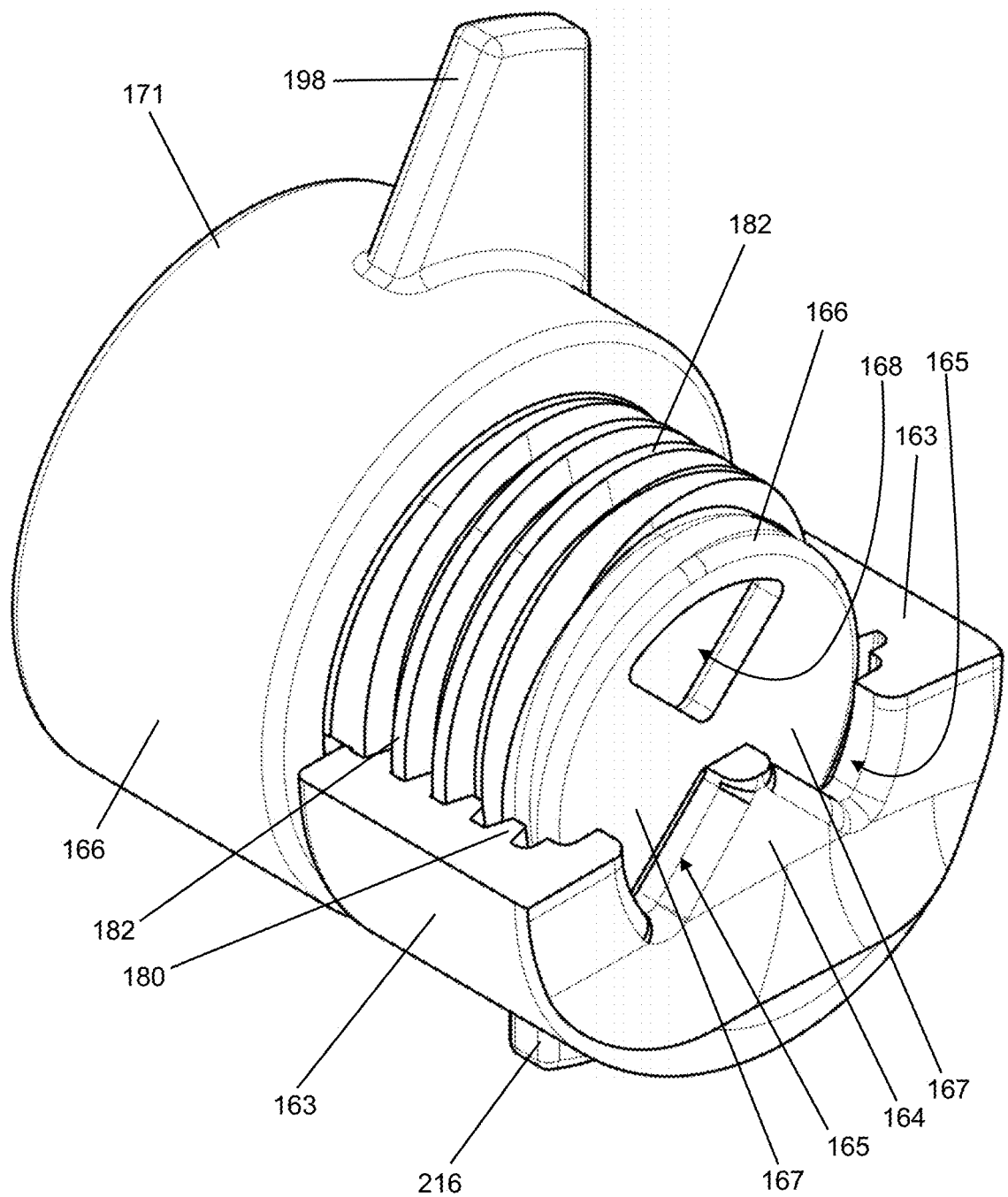
FIG. 26 shows a schematic perspective partial cross-sectional view of the valve according to FIGS. 22 to 25 in the closed state.
Figure 27:
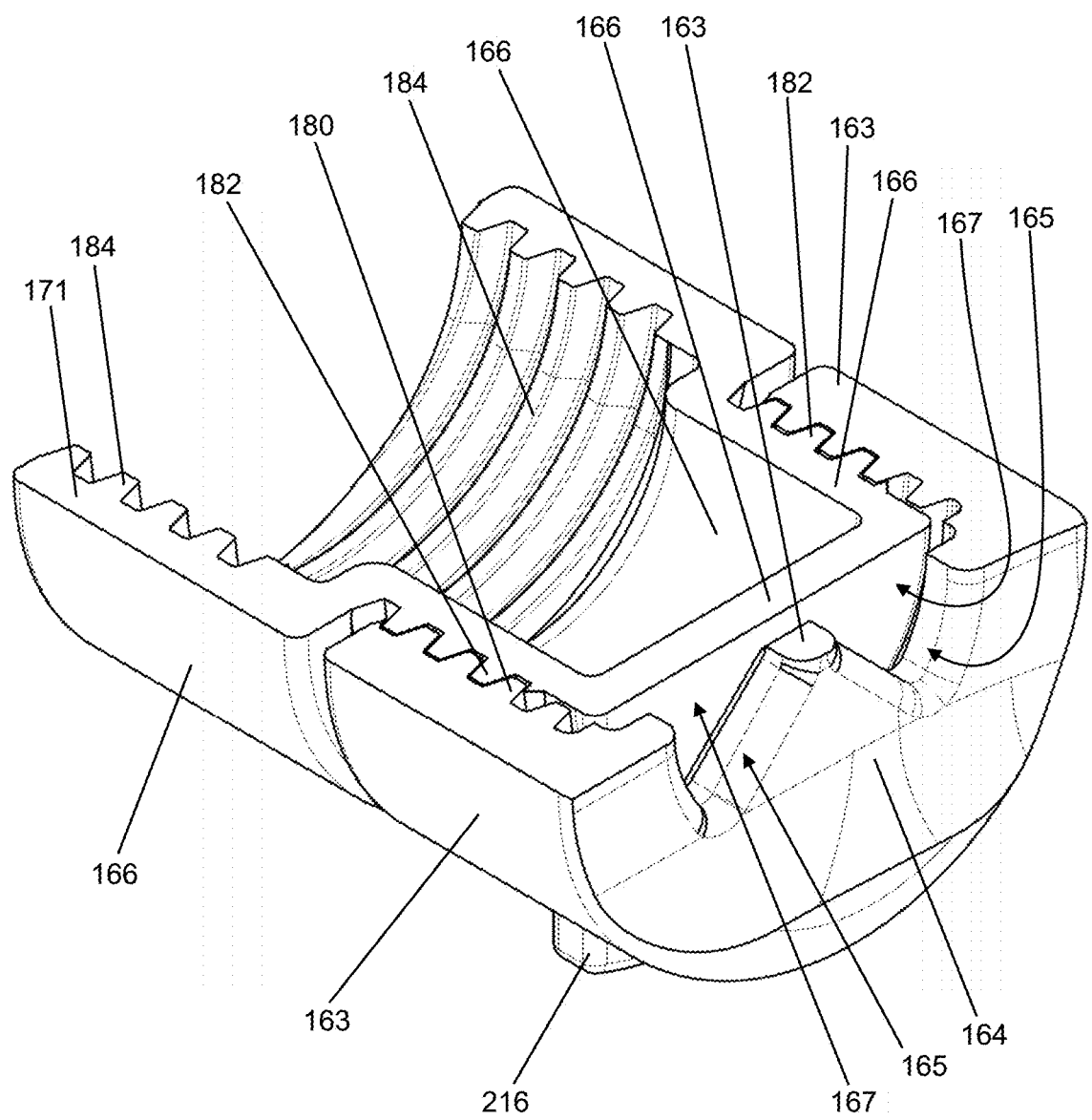
FIG. 27 shows a schematic perspective cross-sectional view of the valve according to FIGS. 22 to 26 in the closed state.
Figure 28:
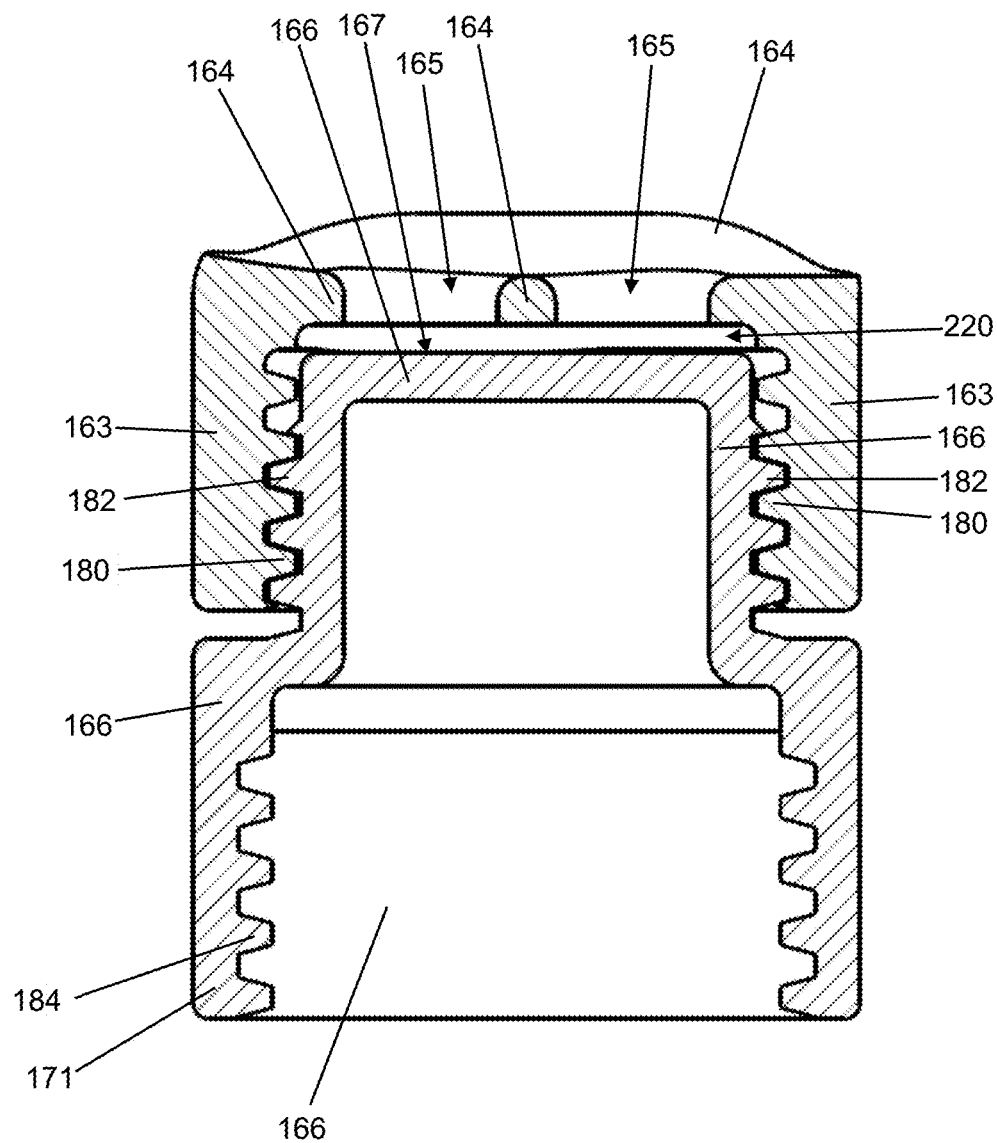
FIG. 28 shows a schematic cross-sectional view of the valve according to FIGS. 22 to 27 in the closed state.

FIGS. 11 to 19 are drawings showing various views of a second exemplary embodiment of a device according to the invention for producing a spacer for a shoulder joint and parts thereof. FIGS. 20 and 21 show a shoulder joint spacer which has been produced using such a second device according to the invention as the result of a method according to the invention, the method steps of which are shown chronologically in FIGS. 12 to 21.

Figure 12:
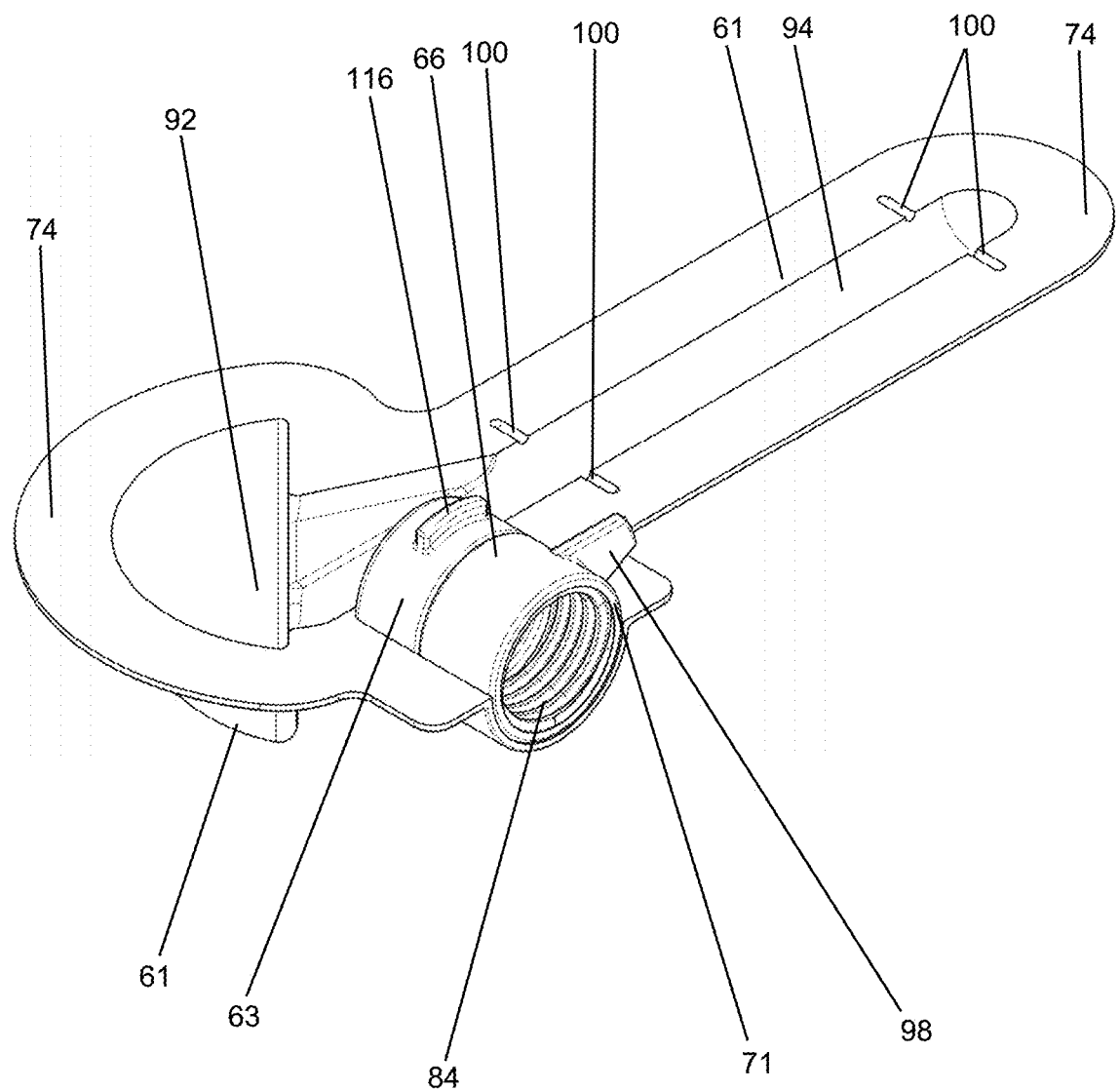
FIG. 12 shows a schematic perspective view of the open second device according to the invention according to FIG. 11 without metal core.
Figure 13:
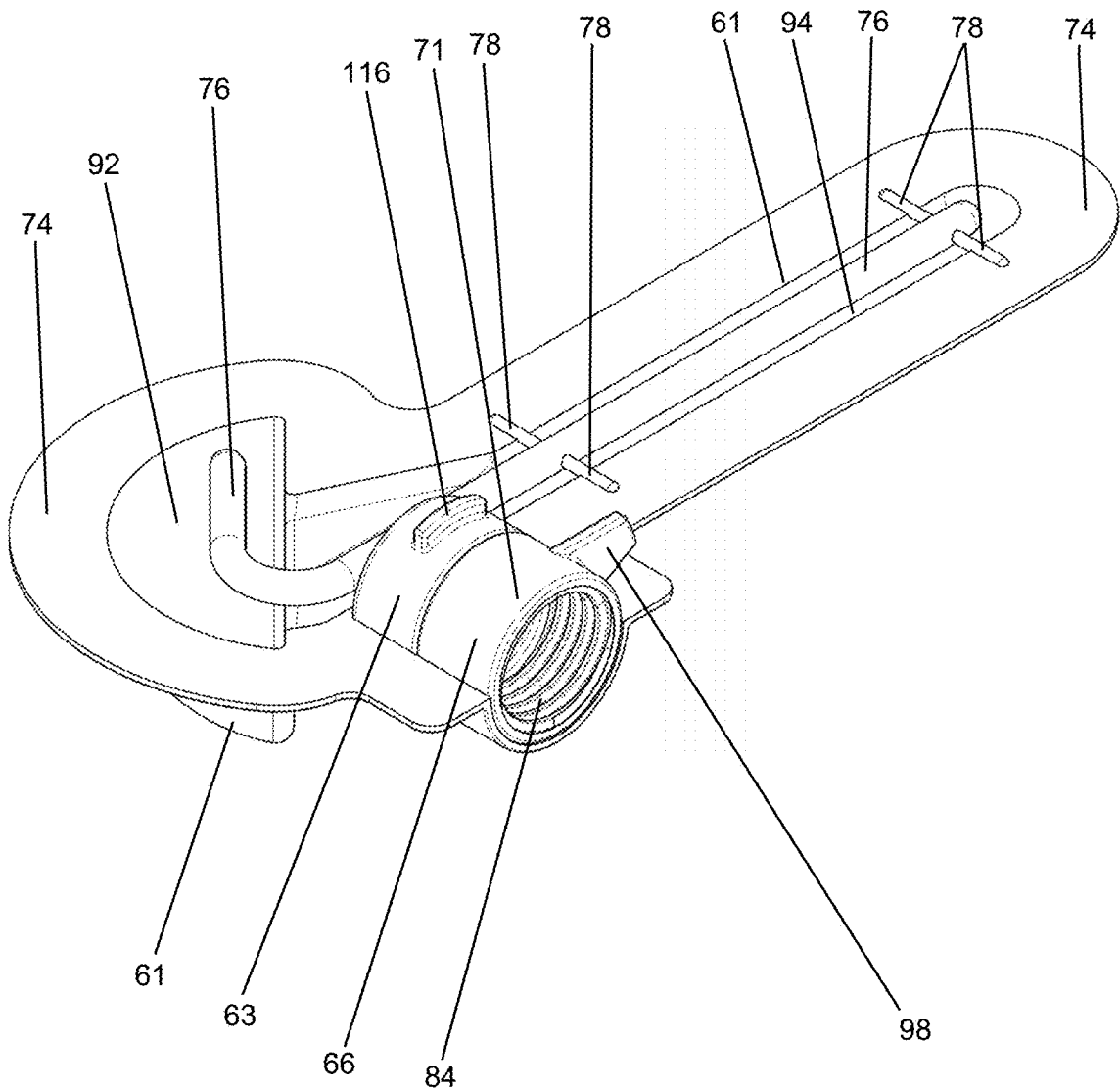
FIG. 13 shows a schematic perspective view of the open second device according to the invention without the second part of the casting mold but with inserted metal core.
Figure 14:
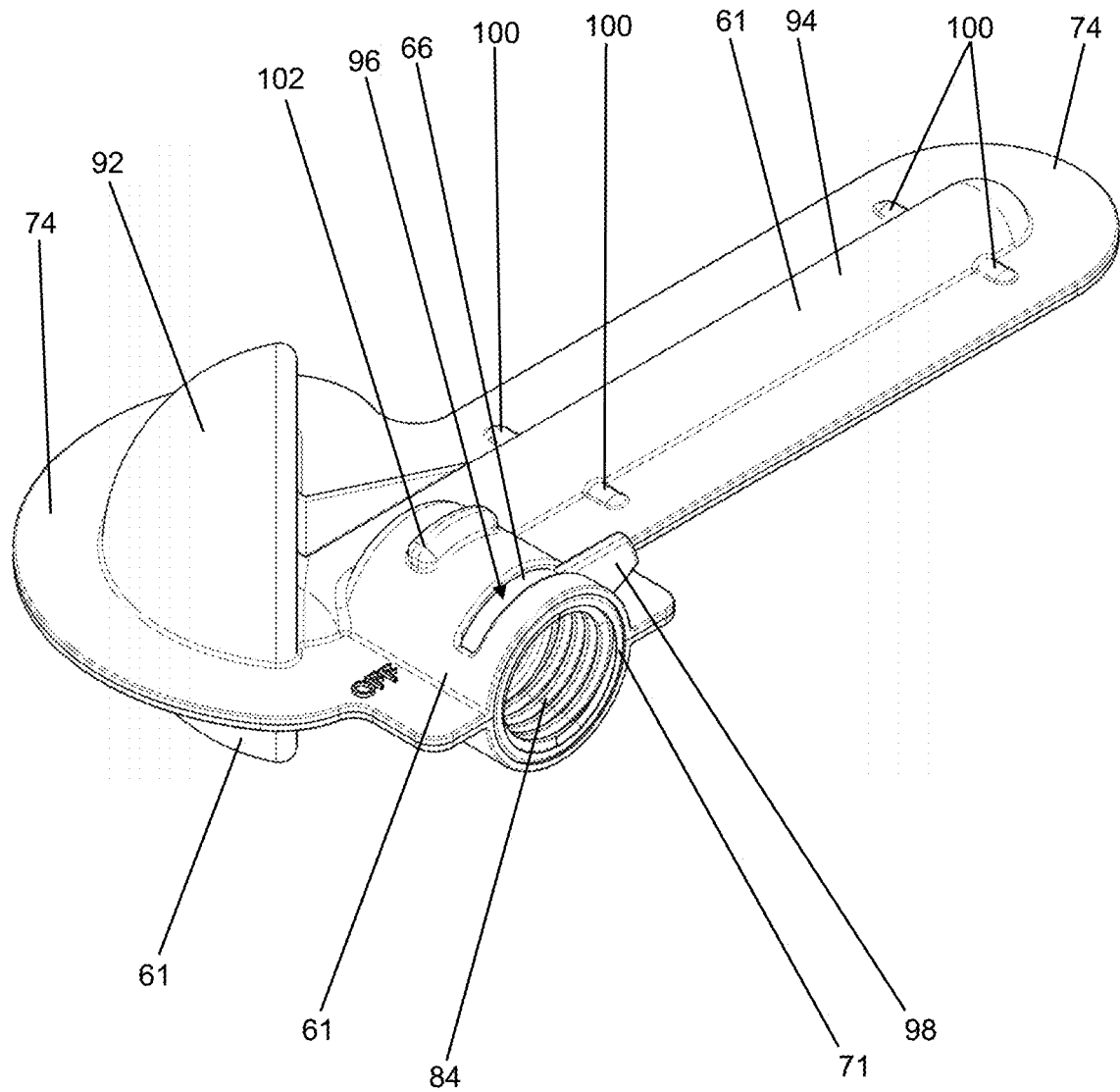
FIG. 14 shows a schematic perspective external view of the closed second device according to the invention according to FIGS. 11 to 13 with the valve open.
Figure 15:
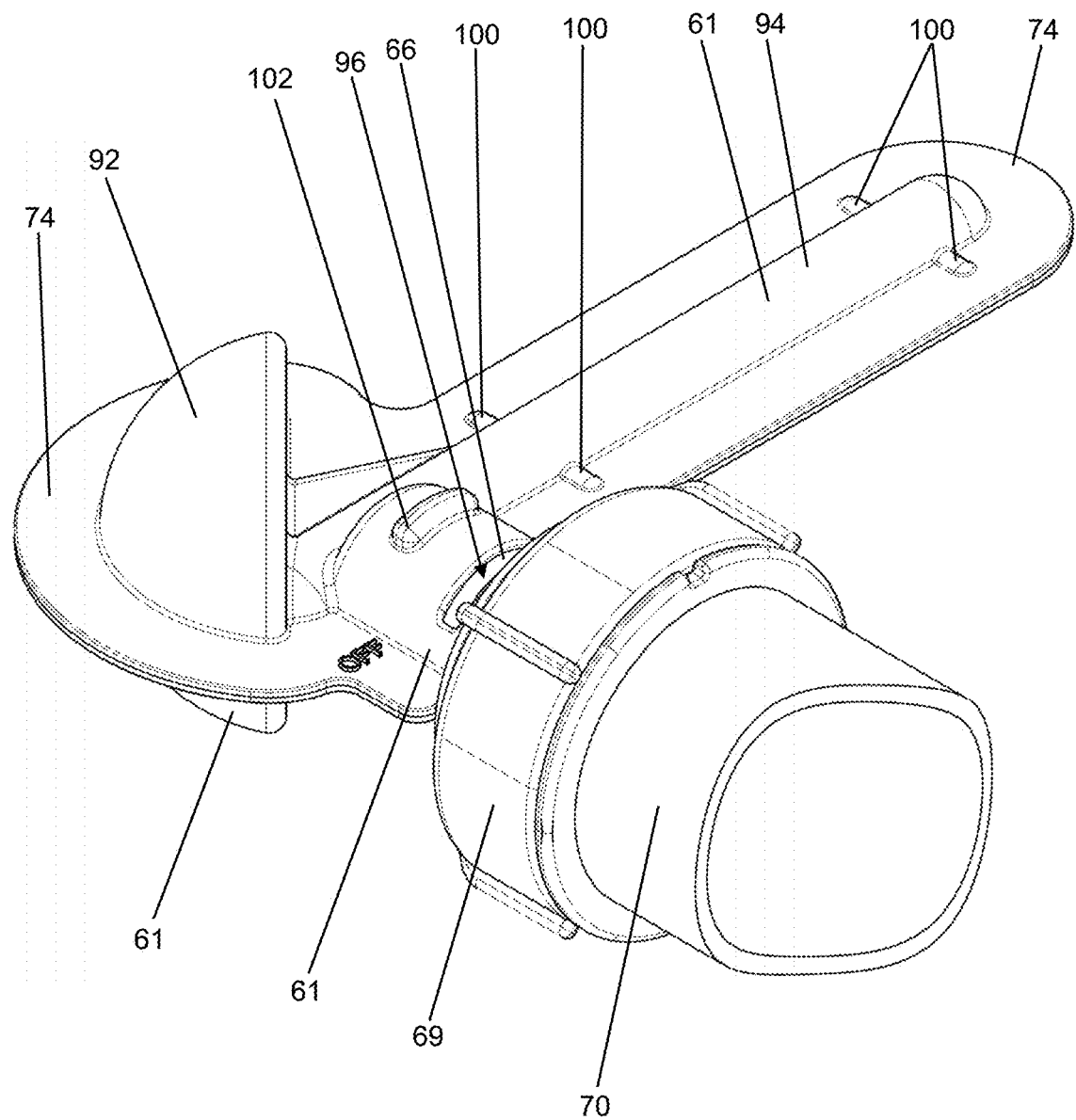
FIG. 15 shows a schematic perspective external view of the closed second device according to the invention according to FIG. 14 with connected bone cement cartridge.
Figure 16:
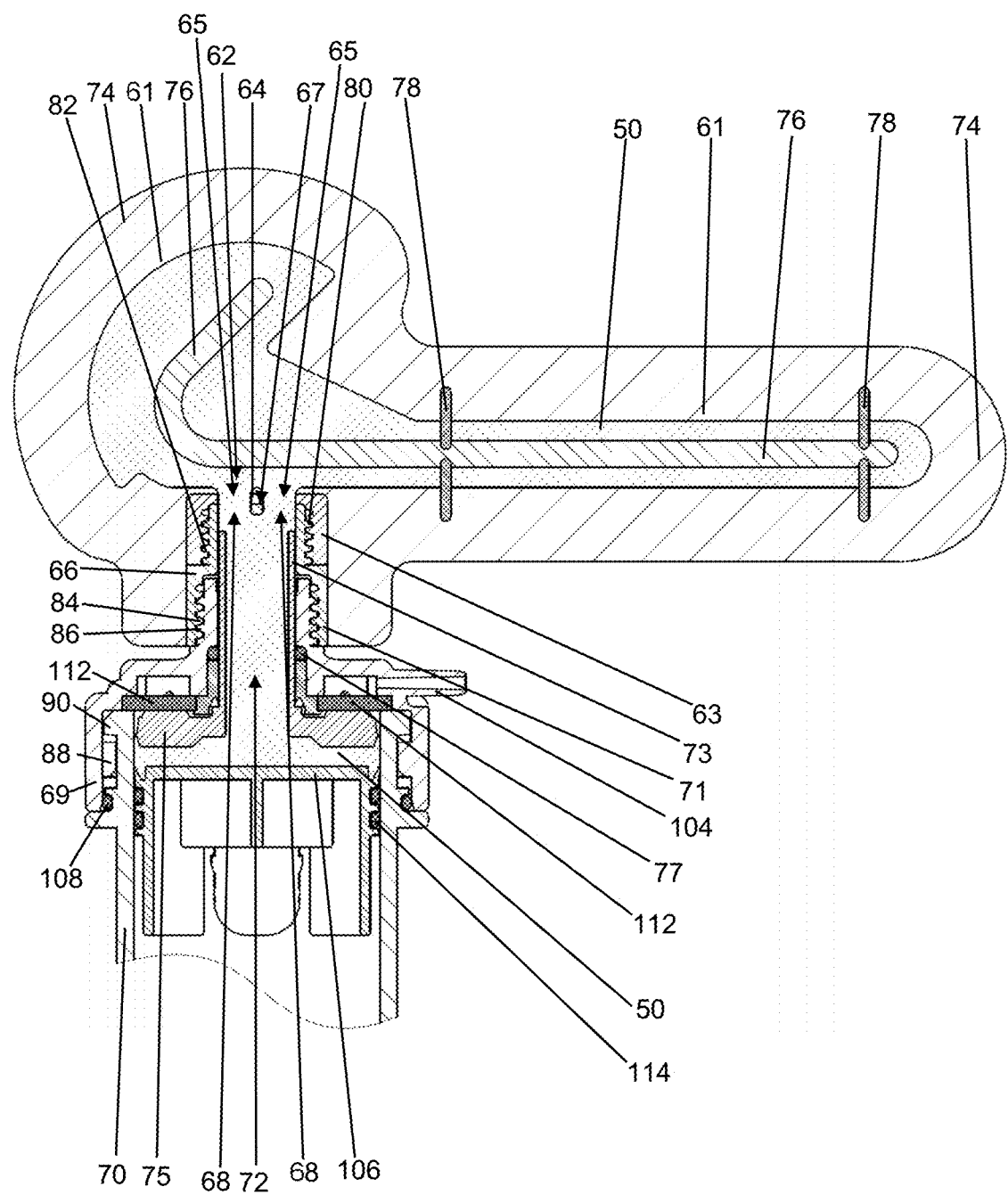
FIG. 16 shows a schematic cross-sectional view of the second device according to the invention with the valve open after the filling of bone cement paste from the bone cement cartridge into a casting mold of the device.
Figure 17:
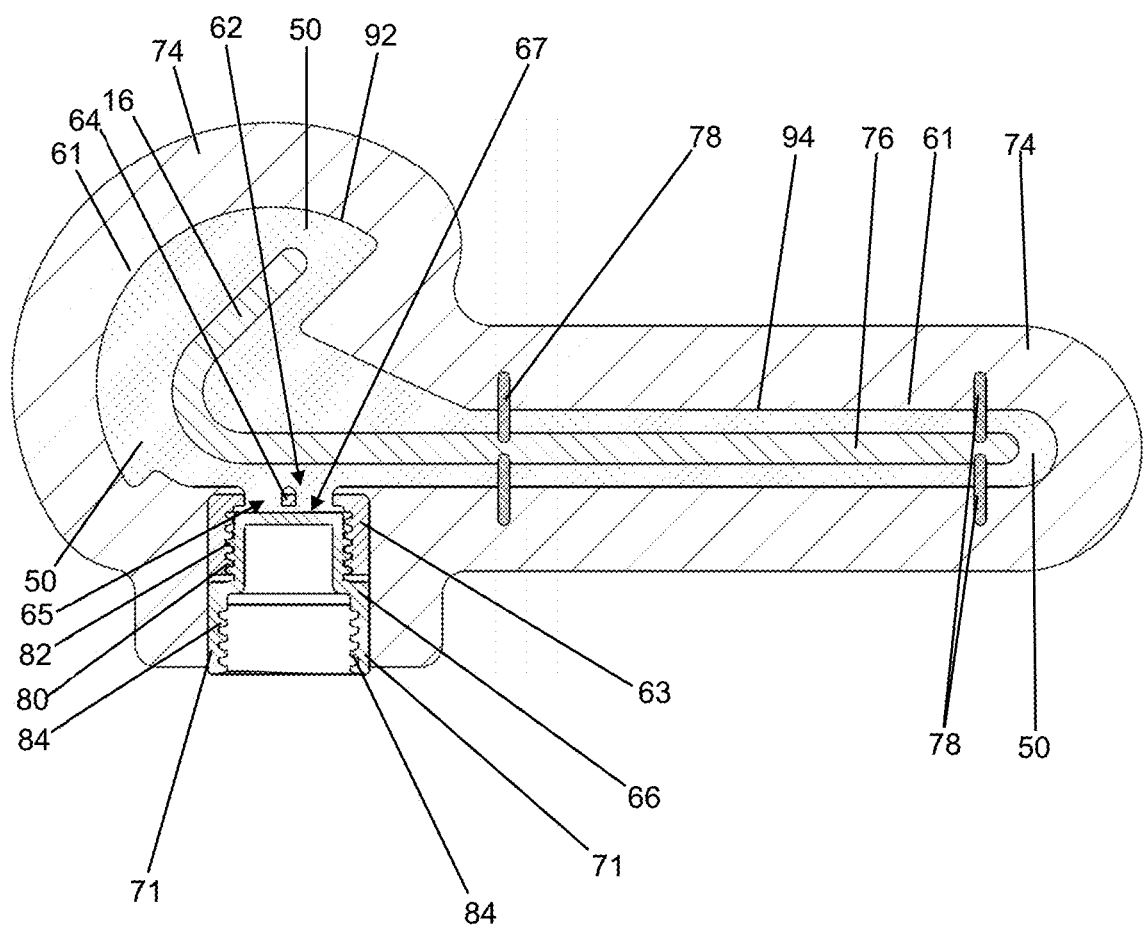
FIG. 17 shows a schematic cross-sectional view of the second device according to the invention with the valve closed after removal of a bone cement cartridge and an adapter element from the casting mold.

The second device according to the invention is suitable and provided for producing a spacer 120 for a shoulder joint. The device comprises a casting mold 61. The casting mold 61 may be constructed in two parts. FIGS. 11 to 13, 16, 17 and 19 in each case show just one of the two parts of the casting mold 61. FIGS. 14, 15 and 18 show both parts of the casting mold 61. A filling opening 62 for the introduction of bone cement paste 50 may be formed on one side of the casting mold 61, which filling opening may be defined in each case in both parts of the casting mold 61 by a semicircular cylindrical opening. A valve seat 63 may be arranged in this filling opening 62. The valve seat 63 may be firmly connected to a part of the casting mold 61, as shown in FIGS. 12 and 13. For better and tighter connection of the valve seat 63 to the casting mold 61, the valve seat 63 may have patterning on its external surface, for example longitudinal grooves, which are arranged parallel to the cylinder axis of a cylindrical outer wall of the valve seat 63.

The valve seat 63 may take the form of a hollow cylinder which, apart from two first feed-throughs 65, is closed on a head side 64 oriented in the direction of the filling opening 62. The two first feed-throughs 65 may be quadrant-shaped and may preferably be arranged rotated relative to one another by 180° with regard to the cylinder axis of the valve seat 63. A valve body 66 may be arranged in the interior of the valve seat 63 so as to be axially rotatable relative to the valve seat 63. The valve body 66 may have a sealing face 67 or surface oriented in the direction of the head side 64 of the valve seat 63. The valve body 66 may be constructed as a stepped hollow cylinder, the front part of which can be screwed or put into the valve seat 63.

Two second feed-throughs 68 may be arranged in the sealing face 67. The two second feed-throughs 68 may, similarly to the first feed-throughs 65, be quadrant-shaped and may preferably be arranged rotated or offset relative to one another by 180° with regard to the cylinder axis of the valve body 66. The valve seat 63 and valve body 66 together form a valve of the device. An adapter element 69 for liquid-tight connection of a bone cement cartridge 70 may be screwed into the valve body 66. The bone cement cartridge 70 and the adapter element 69 may be part of the device according to the invention. The valve body 66 may on its open side, which is remote from the sealing face 67, be formed as a port 71 for connecting the adapter element 69.

The bone cement cartridge 70 may have on its front side a delivery opening 72 for delivering the bone cement paste 50 from the bone cement cartridge 70. The delivery opening 72 is arranged in the adapter element 69. A delivery tube 73 may be located in the interior of the bone cement cartridge 70, which delivery tube is connected in the interior of the bone cement cartridge 70 to a mixer 75. The delivery tube 73 is guided in axially mobile manner in the adapter element 69 and mounted so as to be rotatable. Through movement of the delivery tube 73, the mixer 75 may be moved in the interior of the bone cement cartridge 70 in order to mix the bone cement paste 50 thoroughly in the interior of the bone cement cartridge 70. Prior to fastening of the adapter element 69 to the port 71, the delivery tube 73 may be broken off at a predetermined breaking point. The delivery tube 73 may be sealed relative to the adapter element 69 by way of a circumferential seal 77. The adapter element 69 may close the bone cement cartridge 70 on its front side apart from the delivery opening 72 and optionally apart from a vacuum port 104.

The casting mold 61 can be inexpensively fabricated from plastics film. The plastics film may have a plurality of layers. The two parts of the casting mold 61 may be fastened together via flanges 74. By connecting the two parts of the casting mold 61 via the flanges 74, the casting mold 61 may be closed to the outside. Vent openings (not visible in FIGS. 11 to 19) may be arranged in the casting mold 61. Air or gas can escape through the vent openings from the interior of the closed casting mold 61 when a bone cement paste 50 is filled into the casting mold 61 through the filling opening 62.

A metal core 76 may be placed in the interior of the casting mold 61. The metal core 76 may consist of surgical steel or of titanium. The metal core 76 for the shoulder joint spacer may be a cylindrical body bent into a hook. Alternatively, it would theoretically also be possible to fabricate the metal core 76 from a plastics material such as PMMA. The metal core 76 may be connected to the casting mold 61 via retaining pins 78. The metal core 76 may be spaced from the internal wall of the casting mold 61 with the aid of the retaining pins 78, such that the bone cement paste 50 can flow right around the metal core 76. The metal core 76 brings about stabilization of the spacer 120. The retaining pins 78 may consist of PMMA. This can irreversibly bond to a bone cement paste 50 of PMMA.

The valve seat 63 may have an inner thread 80 on its inside. On the front half of the valve body 66 facing the sealing face 67, the valve body 66 may have on the outside thereof an outer thread 82 matching the inner thread 80 of the valve seat 63. The valve body 66 may be screwed with its outer thread 82 into the inner thread 80 of the valve seat 63.

The first feed-throughs 65 and the second feed-throughs 68 may be brought into overlap with one another by screwing the valve body 66 into the valve seat 63 until the limit stop is reached. The valve is then in the open state. In this open state, a bone cement paste 50 may flow through the first feed-throughs 65 and through the second feed-throughs 68 out of the bone cement cartridge 70 into the casting mold 61. By making a quarter rotation (by 90°) of the valve body 66 relative to the valve seat 63, i.e. by unscrewing the valve body 66 from the valve seat 63, the first feed-throughs 65 and the second feed-throughs 68 may be offset relative to one another, such that the sealing face 67 of the valve body 66 covers the first feed-throughs 65 of the valve seat 63 and the closed regions of the head side 64 of the valve seat 63 cover the second feed-throughs 68 of the valve body 66. The valve is then in the closed state. Due to the small stroke of the valve body 66 relative to the valve seat 63 in the event of a quarter rotation, the gap arising between the valve body 66 and the valve seat 63 is so narrow (less than 1 mm wide) that a bone cement paste 50 of a normal, let alone high, viscosity, is incapable of passing through the gap. This is particularly the case because the bone cement paste 50 is deflected from its actual direction of flow by 90° in the gap.

The reverse side of the valve body 66 may have an inner thread 84 arranged in the port 71. The front side of the adapter element 69 has on its front side an outer thread 86 which matches the inner thread 84. The adapter element 69 may accordingly be screwed into the port 71 of the valve body 66. In this way, a liquid-tight connection can be created between the bone cement cartridge 70 and the valve body 66 and thus into the casting mold 61. The inner thread 80 of the valve seat 63, the outer thread 82 of the valve body 66, the inner thread 84 of the valve body 66 and the outer thread 86 of the adapter element 69 may all have the same direction of rotation, i.e. all these threads are right-hand threads or left-hand threads. As a result, the valve can be opened by screwing the adapter element 69 into the port 71 and continuing to rotate the adapter element 69 in the same direction. At the same time, the valve body 66 also provides a seal relative to the valve seat 63.

The adapter element 69 may be or have been connected via a latching means 88 on the adapter element 69 to a mating latch 90 on a cylindrical wall of the bone cement cartridge 70. A circumferential seal 108 which seals the cylindrical wall of the bone cement cartridge 70 relative to the adapter element 69 may be provided for sealing.

The casting mold 61 may have a joint head molding 92 for forming a head 122 of a spacer 120 and a stem molding 94 for forming a stem 124 of a spacer 120 (see FIGS. 20 and 21). Moreover, an orifice 96 for lever 98 of the valve body 66 may be arranged in the casting mold 61 in the region of the filling opening 62. The lever 98 may be connected to the valve body 66. The valve body 66 can be rotated in the valve seat 63 with the lever 98. The orifice 96 is preferably precisely large enough for the valve body 66 to be rotatable only by a maximum of a quarter rotation relative to the valve seat 63. As a result, with the assistance of the lever 98, the valve can be transferred manually from outside from the open state into the closed state or from the closed state into the open state.

In the region of the flanges 74, shapes 100 may be arranged in the casting mold 61 for cavities, in which shapes the retaining pins 78 may be arranged. Shapes 102 for valve fastening may further be arranged in the casting mold 61 in the walls delimiting the filling opening 62, which shapes are provided for receiving matching projections 116 (see FIGS. 12 and 13) on the cylindrical outside of the valve seat 63. Through engagement of the projections 116 in the shapes 102 for valve fastening, the valve seat 63 cannot be rotated in the filling opening 62 and a stable connection is provided.

A vacuum port 104 which is capable of evacuating an interior of the bone cement cartridge 70 in which the bone cement paste 50 is mixed may be arranged in the adapter element 69. As a result, the bone cement paste 50 can be mixed under a vacuum.

A piston 106 for discharging the bone cement paste 50 from the bone cement cartridge 70 through the valve into the casting mold 61 may be arranged in the cylindrical interior of the bone cement cartridge 70. The piston 106 may to this end be cylindrically shaped on the outside and be sealed relative to the cylindrical interior by means of two circumferential seals 114. By advancing the piston 106, the bone cement paste 50 can be pressed out of the delivery opening 72 of the bone cement cartridge 70 into or through the open valve.

A porous disk 112 may be arranged in the adapter element 69. The porous disk 112 is impermeable to the bone cement paste 50 and its starting components. The vacuum port 104 can be covered by the porous disk 112. This prevents any bone cement powder as a starting component of the bone cement paste 50 from being able to penetrate into the vacuum port 104.

The course of a method according to the invention is shown in FIGS. 12 to 21 with reference to the second device according to the invention. Firstly, the open casting mold 61 is provided. FIG. 12 shows this situation. The metal core 76 may then be positioned with the retaining pins 78 in the casting mold 61. To this end, the retaining pins 78 may be arranged and retained at one end between the two parts of the casting mold 61 in the cavities formed by the shapes 100 and arranged with the other end in matching bores in the metal core 76. FIG. 13 shows this situation.

The casting mold 61 may then be closed. FIG. 14 shows this situation. A bone cement paste 50 can be mixed under a vacuum in the bone cement cartridge 70. The bone cement cartridge 70 can then be screwed with the adapter element 69 into the port 71 of the valve body 66. On screwing in the adapter element 69, the valve can be transferred into the open position by screwing the valve body 66 into the valve seat 63 until the limit stop is reached. FIG. 15 shows this situation.

The bone cement paste 50 is then pressed out of the bone cement cartridge 70 through the valve and through the overlapping first feed-throughs 65 and second feed-throughs 68 into the casting mold 61 by advancing the piston 106. FIG. 16 shows this situation. By closing the valve by manually operating the lever 98 and so rotating the valve body 66 by a quarter rotation relative to the valve seat 63, a new bone cement cartridge 70 can be attached at intervals if the volume of the bone cement paste 50 from a single bone cement cartridge 70 is not enough to fill the casting mold 61 completely. The bone cement paste 50 contained in the casting mold 61 cannot flow back out again since the first passages 65 and the second passages 68 are covered in the closed position of the valve and the gap therebetween is insufficient for the viscous bone cement paste 50 to be able flow through.

At some point, the casting mold 61 is filled with the bone cement paste 50. Air or gas has escaped from the casting mold 1 through vent openings in the casting mold 61. By closing the valve with the lever 98, the bone cement paste 50 is sheared or cut off. The bone cement cartridge 70 can be unscrewed and removed. Any remaining thin connections simply tear or break away. FIGS. 17 and 18 show this situation.

In this state, the bone cement paste 50 can be cured in the casting mold 61. FIG. 19 shows this situation. Then, the spacer 120 formed in this way is removed from the casting mold 1. FIG. 20 shows the removed spacer 120. The projecting retaining pins 78 may be cut off. FIG. 21 shows this situation. Any sprue 126 caused by the valve seat 63 and the first passages 65 can likewise be cut off and removed. Points caused by the vent openings may also be removed. The surface of the spacer 120 can be polished and/or coated, for example with antibiotics.

Instead of a casting mold 61 for molding a shoulder joint spacer, it is also straightforwardly possible to use a casting mold for molding a different spacer.

FIGS. 22 to 28 show a valve for a device according to the invention for producing a spacer in the open position (FIGS. 22 to 24) and in the closed position (FIGS. 25 to 28). The valve corresponds to the valves of the first device according to the invention according to FIGS. 1 to 10 and of the second device according to the invention according to FIGS. 11 to 19, but may also be used with other casting molds to produce other spacers.

The valve has a valve seat 163, which may be arranged in a filling opening of a casting mold (not shown). The valve seat 163 may be firmly connected to a part of the casting mold. For better and tighter connectability of the valve seat 163 to a casting mold, the valve seat 163 may have patterning on its external surface, for example longitudinal grooves, which are arranged parallel to the cylinder axis of a cylindrical outer wall of the valve seat 163.

The valve seat 163 may take the form of a hollow cylinder which, apart from two first feed-throughs 165, is closed on a head side 164. The two first feed-throughs 165 may be quadrant-shaped and may preferably be arranged rotated relative to one another by 180° with regard to the cylinder axis of the valve seat 163. A valve body 166 may be arranged in the interior of the valve seat 163 so as to be axially rotatable relative to the valve seat 163. The valve body 166 may have a sealing face 167 or surface oriented in the direction of the head side 164 of the valve seat 163. The valve body 166 may be constructed as a stepped hollow cylinder, the front part of which can be screwed or put into the valve seat 163.

Two second feed-throughs 168 may be arranged in the sealing face 167. The two second feed-throughs 168 may, similarly to the first feed-throughs 165, be quadrant-shaped and may preferably be arranged rotated or offset relative to one another by 180° with regard to the cylinder axis of the valve body 166. The valve seat 163 and valve body 166 together form the valve of a device according to the invention. An adapter element (not shown) for liquid-tight connection of a bone cement cartridge (not shown) may be screwed into the valve body 166. The valve body 166 may on its open side, which is remote from the sealing face 167, be formed as a port 171 for connecting an adapter element.

The valve seat 163 may have an inner thread 180 on its inside. On the front half of the valve body 166 facing the sealing face 167, the valve body 166 may have on the outside thereof an outer thread 182 matching the inner thread 180 of the valve seat 163. The valve body 166 may be screwed with its outer thread 182 into the inner thread 180 of the valve seat 163.

The first feed-throughs 165 and the second feed-throughs 168 may be brought into overlap with one another by screwing the valve body 166 into the valve seat 163 until the limit stop is reached. The valve is then in the open state. In this open state (see FIGS. 22 to 24), a bone cement paste may flow through the first feed-throughs 165 and through the second feed-throughs 168. By making a quarter rotation (by 90°) of the valve body 166 relative to the valve seat 163, i.e. by unscrewing the valve body 166 from the valve seat 163, the first feed-throughs 165 and the second feed-throughs 168 may be offset relative to one another, such that the sealing face 167 of the valve body 166 covers the first feed-throughs 165 of the valve seat 163 and the closed regions of the head side 164 of the valve seat 163 cover the second feed-throughs 168 of the valve body 166. The valve is then in the closed state (see FIGS. 25 to 28). Due to the small stroke of the valve body 166 relative to the valve seat 163 in the event of a quarter rotation, the gap 220 arising between the valve body 166 and the valve seat 163 is so narrow (less than 1 mm wide) that a bone cement paste of a normal, let alone high, viscosity, is incapable of passing through the gap 220 (see FIG. 28). This is particularly the case because the bone cement paste is deflected from its actual direction of flow by 90° in the gap 220. A projection 216 may be provided in order to ensure more stable, non-rotatable connection of the valve seat 163 to the casting mold.

The reverse side of the valve body 166 may have an inner thread 184 arranged in the port 171. An adapter element (not shown) may accordingly be screwed into the port 171 of the valve body 166. The inner thread 180 of the valve seat 163, the outer thread 182 of the valve body 166 and the inner thread 184 of the valve body 166 may all have the same direction of rotation, i.e. all these threads are right-hand threads or left-hand threads. As a result, the valve can be opened by screwing an adapter element into the port 171 and continuing to rotate the adapter element in the same direction. At the same time, the valve body 166 also provides a seal relative to the valve seat 163.

Furthermore, a lever 198 may be arranged on the valve body 166. The valve body 166 can be rotated in the valve seat 163 with the lever 198. As a result, with the assistance of the lever 198, the valve can be transferred manually from outside from the open state into the closed state or from the closed state into the open state.

The features of the invention disclosed in the preceding description, as well as in the claims, figures and exemplary embodiments, may be essential both individually and in any combination for realizing the invention in its various embodiments.

LIST OF REFERENCE NUMBERS

1, 61 Casting mold
 2, 62 Filling opening
 3, 63, 163 Valve seat
 4, 64, 164 Head side
 5, 65, 165 Feed-through
 6, 66, 166 Valve body
 7, 67, 167 Sealing face
 8, 68, 168 Feed-through
 9, 69 Adapter element
 10, 70 Bone cement cartridge
 11, 71, 171 Port
 12, 72 Delivery opening
 14, 74 Flange
 16, 76 Metal core
 18, 78 Retaining pin
 20, 80, 180 Inner thread 22, 82, 182 Outer thread
24, 84, 184 Inner thread
26, 86 Outer thread
28, 88 Latching means
30, 90 Mating latch
32, 92 Joint head molding
34, 94 Stem molding
36, 96 Orifice
38, 98, 198 Lever
40, 100 Shape for cavities
42, 102 Shape for valve fastening
44, 104 Vacuum port
46, 106 Piston
48, 108 Seal
50 Bone cement paste
52, 112 Porous disk
54, 114 Seal
56, 116, 216 Projection
58 Bore
73 Delivery tube
75 Mixer
77 Seal
120 Spacer
122 Head
124 Stem
126 Sprue
220 Gap

We claim:

1. A device for producing a spacer by curing bone cement paste,
   wherein the spacer is provided in the medical field for replacing a joint or part of a joint comprising an articulating surface of the joint, or for replacing a hip joint or a shoulder joint, the device having
   a casting mold for molding the spacer from bone cement paste, the casting mold having at least one filling opening for introducing the bone cement paste;
   a valve seat, the valve seat being connected to the casting mold in the region of the at least one filling opening, wherein the valve seat has, at least in places, a closed head side with at least one first feed-through, wherein the at least one first feed-through opens into the at least one filling opening;
   a valve body mounted so as to be rotatable relative to the valve seat and which has a sealing face, wherein the sealing face is oriented in the direction of the closed head side of the valve seat, wherein at least one second feed-through is arranged in the sealing face;
   wherein the valve seat and the valve body together form a valve, wherein the valve is reversibly transferable into an open position and into a closed position by rotation of the valve body relative to the valve seat, wherein, in the open position of the valve, the at least one first feed-through of the valve seat and the at least one second feed-through of the valve body are located above one another at least in places and provide a connection permeable to bone cement through the valve into the casting mold, wherein, in the closed position of the valve, the at least one first feed-through of the valve seat is covered by the sealing face of the valve body, wherein, in the closed position of the valve, the at least one filling opening of the casting mold is covered and closed for bone cement paste and wherein the valve is connected on the side remote from the casting mold to a port for liquid-tight connection of a bone cement cartridge or the valve has the port, and wherein at least one vent opening is provided in the casting mold, through which air or gas can escape from the interior of the casting mold.

2. The device according to claim 1, characterized in that the valve seat is connected to the casting mold so as not to be rotatable relative to the casting mold, and is rigidly connected to the casting mold.

3. The device according to claim 1, characterized in that the valve is manually operable from outside the device, wherein the valve body is manually rotatable relative to the valve seat and the valve is transferable by rotation from the closed position into the open position and from the open position into the closed position.

4. The device according to claim 1, characterized in that, in the closed position of the valve, the at least one first feed-through of the valve seat is covered by the sealing face of the valve body, wherein the closed head side of the valve seat and the sealing face of the valve body are spaced apart from one another by a maximum of 2 mm.

5. The device according to claim 1, characterized in that the valve body is mounted so as to be rotatable about an axis of rotation relative to the valve seat, wherein the axis of rotation extends perpendicular to the sealing face of the valve body or wherein the axis of rotation extends along an axis of rotational symmetry of the sealing face of the valve body.

6. The device according to claim 1, characterized in that the valve body has the port for liquid-tight connection of a bone cement cartridge or is firmly connected to such a port.

7. The device according to claim 1, characterized in that the device has an adapter element which is connected or connectable to the bone cement cartridge, wherein the adapter element is detachably and interlockingly connected or connectable to the port, such that an interior of the bone cement cartridge is connected or connectable permeably for bone cement paste via the adapter element to the at least one second feed-through in the valve body.

8. The device according to claim 1, characterized in that the device comprises the bone cement cartridge for mixing bone cement starting components and for delivering mixed bone cement paste from the bone cement cartridge or comprises the bone cement cartridge for mixing polymethyl methacrylate bone cement starting components and for delivering mixed polymethyl methacrylate bone cement paste from the bone cement cartridge, wherein the bone cement cartridge contains the bone cement starting components for producing the bone cement in mutually separate regions.

9. The device according to claim 1, characterized in that the casting mold consists of a plastics film or
   the casting mold is constructed from two or more plastics films, which are welded or adhesively bonded together, and wherein the casting mold is fabricated from PETG film and/or polyamide film and/or PE film.

10. The device according to claim 1, characterized in that a sum of all the openings of the at least one first feed-through in the closed head side is at most as large as the closed surface of the head side and
    a sum of all the openings of the at least one second feed-through in the sealing face is at most as large as the closed surface of the sealing face.

11. The device according to claim 1, characterized in that the valve seat has an inner thread on an inside and the valve body has a matching outer thread on an outside, such that the valve body is able to be screwed into the valve seat.

12. The device according to claim 11, characterized in that the inner thread in the valve body or the outer thread on the valve body is a right-hand thread and the valve is transferable from the closed to the open position by equidirectional rightward rotation of the valve body and the valve is transferable from the open to the closed position by contradirectional leftward rotation of the valve body or the inner thread in the valve body or the outer thread on the valve body is a left-hand thread and the valve is transferable from the closed to the open position by equidirectional leftward rotation of the valve body and the valve is transferable from the open to the closed position by contradirectional rightward rotation of the valve body or the inner thread of the valve seat and the inner thread and the outer thread of the valve body are all left-hand threads or all right-hand threads, wherein an outer thread of an adapter element also has the same direction of rotation for liquid-tight connection of the bone cement cartridge to the port.

13. The device according to claim 1, characterized in that the port comprises, for liquid-tight connection of the bone cement cartridge, an inner thread in the valve body or an outer thread on the valve body, wherein an adapter element of the bone cement cartridge or on the bone cement cartridge has a mating thread matching the inner thread or the outer thread.

14. The device according to claim 1, characterized in that the at least one first feed-through in the closed head side has the same size and shape as the at least one second feed-through in the sealing face and/or the at least one first feed-through in the closed head side is two first feed-throughs and the at least one second feed-through in the sealing face is two second feed-throughs.

15. The device according to claim 1, characterized in that a collar is arranged on the sealing face of the valve body, and the collar rests on an edge of the valve seat or the collar is arranged on the closed head side of the valve seat and rests on an edge of the valve body.

16. The device according to claim 1, characterized in that a lever is arranged on the valve body, wherein the lever has a radial extent with regard to an axis of rotation of the valve body, wherein the lever projects through an orifice in the casting mold or in the valve seat, wherein the orifice in the casting mold is optionally arranged in the region of the connection to the valve seat, wherein the orifice is dimensioned such that the valve may be transferred from the open position into the closed position and vice versa by rotation of the valve body in the valve seat by means of the lever, and wherein the orifice is dimensioned such that the valve body may be rotated by a maximum of 90° relative to the valve seat.

17. The device according to claim 1, characterized in that the valve body and the valve seat are fabricated of plastic, or of a thermoplastic, wherein the valve seat is adhesively bonded or welded to a wall of the casting mold.

18. The device according to claim 1, characterized in that the casting mold has at least three cavities, starting from an inner chamber of the casting mold, for receiving retaining pins, wherein the casting mold comprises two parts and the cavities are arranged in edges or flanges of at least one part of the two-part casting mold; or the casting mold has four cavities, starting from an inner chamber of the casting mold, for receiving retaining pins, wherein the casting mold comprises two parts and the cavities are arranged in edges or flanges of at least one part of the two-part casting mold.

19. The device according to claim 1, characterized in that the device has a metal core for arrangement in the casting mold, wherein the metal core has bores for receiving retaining pins, wherein the bores are not arranged in a region of the casting mold for molding a sliding surface of the spacer, the bores being arranged in a region of the casting mold for molding a stem of the spacer.

20. The device according to claim 1, characterized in that at least one of the at least one vent opening is arranged in a region of the casting mold which forms a sliding surface or a joint head of the spacer.

21. The device according to claim 1, characterized in that the at least one first feed-through in the in areas closed head side is two first feed-throughs and the at least one second feed-through in the sealing face is two second feed-throughs, wherein the two first feed-throughs are arranged in the valve seat in quadrants arranged opposingly with regard to the axis of rotation of the valve body and the two second feed-throughs are arranged in the sealing face in quadrants arranged opposingly with regard to an axis of rotation of the valve body.

22. A method for producing a spacer for replacing a joint or part of a joint, in particular a hip joint or a shoulder joint, comprising an articulating surface of the joint, wherein the method is carried out with the device according to claim 1, the method having the following chronological steps:

A) connecting a bone cement cartridge to the port of the device in liquid-tight manner;

B) injecting bone cement paste from the bone cement cartridge through the valve in the open position into the casting mold;

C) rotating the valve body relative to the valve seat and so transferring the valve into the closed position and shearing off the bone cement paste at the at least one first feed-through in the closed head side of the valve seat by rotating the valve body relative to the valve seat;

D) detaching the bone cement cartridge from the port;

E) curing the bone cement paste in the casting mold; and

F) removing the resultant molded and cured spacer from the casting mold.

23. The method according to claim 22, characterized in that the following intermediate steps proceed after step D) and before step E):

D2) connecting a new bone cement cartridge to the port of the device in liquid-tight manner, wherein bone cement paste or starting components for producing the bone cement paste is/are present in the new bone cement cartridge;

D3) rotating the valve body relative to the valve seat and so transferring the valve into the open position;

D4) injecting the bone cement paste from the new bone cement cartridge through the valve in the open position into the casting mold;

D5) rotating the valve body relative to the valve seat and so transferring the valve into the closed position and shearing off the bone cement paste at the at least one first feed-through in the closed head side of the valve seat by rotating the valve body relative to the valve seat; and D6) detaching the new bone cement cartridge from the port.

24. The method according to claim 22, characterized in that the bone cement paste is mixed before step B), in the bone cement cartridge from a monomer liquid and a cement powder, wherein, optionally before step D3) and before step D2), the bone cement paste is mixed in the new bone cement cartridge from a monomer liquid and a cement powder.

25. The method according to claim 22, characterized in that the bone cement cartridge and/or the new bone cement cartridge is screwed into the port for liquid-tight connection of the bone cement cartridge and/or the new bone cement cartridge to the port and, for detaching the bone cement cartridge and/or the new bone cement cartridge from the port, the bone cement cartridge or the new bone cement cartridge is unscrewed from the port.

26. The method according to claim 22, characterized in that the valve body is rotated relative to the valve seat by screwing the valve body in the valve seat or by manually rotating the valve body relative to the valve seat, wherein manual rotation proceeds by operation of a lever extending radially away from the valve body and extending through an orifice in the casting mold or in the valve seat.

27. The method according to claim 22, characterized in that injection of the bone cement paste from the bone cement cartridge or the new bone cement cartridge proceeds by pushing a piston into an interior of the bone cement cartridge.

28. The method according to claim 22, characterized in that a metal core is arranged within the casting mold before step B), wherein the metal core is spaced from an internal wall of the casting mold via a plurality of retaining pins, wherein the plurality of retaining pins are fastened in bores in the metal core and in cavities for receiving retaining pins in the internal wall of the casting mold.

29. The method according to claim 23, characterized in that steps D2) to D6) are repeated once or multiple times with in each case new bone cement cartridges which contain bone cement paste or the starting components thereof until the casting mold is filled completely or as required with bone cement paste.

* * * * *